US006660498B1

(12) United States Patent
Hui et al.

(10) Patent No.: US 6,660,498 B1
(45) Date of Patent: Dec. 9, 2003

(54) MALARIA IMMUNOGENIC COMPOSITION

(75) Inventors: George S. N. Hui, Honolulu, HI (US); Lap-Yin Pang, Kwai Chung (HK); Walter K. K. Ho, Taipo (HK)

(73) Assignees: University of Hawaii, Honolulu, HI (US); The Chinese University of Hong Kong, Hong Kong (HK); Queen Emma Foundation, Honolulu, HI (US)

( * ) Notice: Subject to any disclaimer, the term of this patent is extended or adjusted under 35 U.S.C. 154(b) by 0 days.

(21) Appl. No.: 09/710,000

(22) Filed: Nov. 10, 2000

(65) Prior Publication Data

(65)

Related U.S. Application Data

(60) Provisional application No. 60/165,178, filed on Nov. 12, 1999, provisional application No. 60/168,327, filed on Dec. 1, 1999, and provisional application No. 60/226,861, filed on Aug. 22, 2000.

(51) Int. Cl.$^7$ .......................... C12P 21/06; C12N 15/09; A23J 1/00; C07K 1/00; C07K 14/00
(52) U.S. Cl. ..................... 435/69.1; 435/69.3; 530/412; 530/413; 530/414; 530/415; 530/416; 530/417
(58) Field of Search .......................... 424/184.1, 265.1, 424/266.1, 269.1, 272.1; 435/69.1, 69.3; 530/412, 413, 414, 415, 416, 417

(56) References Cited

U.S. PATENT DOCUMENTS

| | | | |
|---|---|---|---|
| 5,110,729 A | | 5/1992 | Maeda et al. |
| 5,194,376 A | * | 3/1993 | Kang |
| 5,720,959 A | | 2/1998 | Holder et al. |
| 5,891,435 A | * | 4/1999 | Muir et al. |
| 2002/0076403 A1 | * | 6/2002 | Longacre-Andre et al. |

FOREIGN PATENT DOCUMENTS

| | | |
|---|---|---|
| WO | 97/30158 | 8/1997 |
| WO | 98/45324 | 10/1998 |

OTHER PUBLICATIONS

S. P. Chang et al., "Generalized immunological recognition of the major merozoite surface antigen (gp195) of Plasmodium falciparum", *Proc. Natl. Acad. Sci. USA* vol. 86, pp. 6343–6347, Aug. 1989, Medical Sciences.

S. P. Chang, "Expression Systems That Best Mimic Native Structure Which Ones to Try First and Why", *Am. J. Trop. Med. Hyg.*, 50(4) Suppl. 1994, pp. 11–19.

S. P. Chang et al., "A Recombinant Baculovirus 42–Kilodalton C–Terminal Fragment of *Plasmodium falciparum* Merozoite Surface Protein 1 Protects Aotus Monkeys against Malaria", *Infection and Immunity*, Jan. 1996, pp. 253–261.

S. P. Chang et al., "A Carboxyl–Terminal Fragment of *Plasmodium flaciparum* gp195 Expressed by a Recombinant Baculovirus Induces Antibodies That Completely Inhibit Parasite Growth", *The Journal of Immunology*, vol. 149, No. 2, Jul. 15, 1992, pp. 548–555.

A. Cheung et al., "Immunization with synthetic peptides of a *Plasmodium falciparum* surface antigen induces antimerozoite antibodies", *Proc. Natl. Acad. Sci. USA*, vol. 83, Nov. 1986, Medical Sciences, pp. 8328–8332.

H. M. Etlinger et al., "Ability of Recombinant or Native Proteins To Protect Monkeys against Heterologous Challenge with *Plasmodium falciparum*", *Infection and Immunity*, Oct. 1991, pp. 3498–3503.

G. S. N. Hui et al., "Serum from Pf195 Protected Aotus Monkeys Inhibit *Plasmodium falciparum* Growth in Vitro", Research Brief, Experimental Parasitology 64, 519–522 (1987).

G.S.N. Hui et al., "Roles of Conserved and Allelic Regions of the Major Merozoite Surface Protein (gp195) in Immunity against *Plasmodium falciparum*", *Infection and Immunity*, Apr. 1992, pp. 1422–1433.

G. S. N. Hui et al., "Immunological Cross–Reactivity of the C–Terminal 42–Kilodalton Fragment of *Plasmodium falciparum* Merozoite Surface Protein 1 Expressed in Baculovirus", *Infection and Immunity*, Aug. 1993, pp. 3403–3411.

G. S. N. Hui et al., "Dominance of Conserved–B–Cell Epitopes of the *Plasmodium falciparum* Merozoite Surface Protein, MSPI, in Blood–Stage Infections of Naïve Aotus Monkeys", *Infection and Immunity*, May 1996, pp. 1502–1509.

(List continued on next page.)

*Primary Examiner*—Mark Navarro
(74) *Attorney, Agent, or Firm*—Morrison & Foerster LLP

(57) ABSTRACT

We utilized the silkworm (*Bombyx mori*)/baculovirus system to produce recombinant Major Merozoite Surface Protein 1 (MSP1$_{42}$) because of the low cost and potential high yield of this expression system. The MSP1$_{42}$ (3D7 sequence) was cloned into the baculovirus, BmNPV with the melittin signal sequence. The recombinant virus, BmNPV-Sp42 was used to infect silkworms for the expression of MSP1$_{42}$ (Sp42). One recombinant clone expressed high level of Sp42 with an estimated 0.5 mg of antigen produced within a single worm. The Sp42 was recognized by monoclonal and polyclonal antibodies specific for parasite MSP1 in direct binding and competitive binding ELISAs, suggesting that Sp42 possesses antigenic determinants similar to parasite MSP1$_{42}$. Immunogenicity studies were performed in rabbits. Sp42 induced high titers of antibodies crossreactive with MSP1. Specificity analyses showed that anti-Sp42 antibodies reacted primarily against conserved determinants on MSP1-19. Our results showed that the silkworm expression system can produce recombinant MSP1$_{42}$ that are antigenically and immunogenically comparable to other recombinant MSP1 antigens expressed in other eukaryotic systems. The low cost ad high level of protein expression makes it an attractive alternative for the development of a human malaria vaccine.

10 Claims, 4 Drawing Sheets

OTHER PUBLICATIONS

G. S. N. Hui et al., "Immunogenicity of the C-Terminal 19-kDa Fragment of the *Plasmodium falciparum*", Dept. of Tropical Medicine, Univ. of Hawaii, *The Journal of Immunology*, 1994, pp. 2544–2553.

D. C. Kaslow et al., "Expression and antigenicity of *Plasmodium falciparum* major merozoite surface protein (MSP1$_{19}$) variants secreted from *Saccharomyces cerevisiae*", *Molecular and Biochemical Parasitology 63* (1994) 283–289.

"Insect Cell Biotechnology", ed. by K. Maramorosch et al., 1994, by CRC Press, Inc. 31 pgs.

L. H. Miller et al., "Research Toward Malaria Vaccines", *Science*, vol. 234, Dec. 1986, pp. 1349–1356.

L. H. Miller et al., "Analysis of sequence diversity in the *Plasmodium falciparum* merozoite surface protein–1 (MSP–1)", *Molecular and Biochemical Parasitology*, 59 (1993), 14 pgs.

J. Mitsuhashi, "Invertebrate Cell System Applications", vol. 1, 1989, CRC Press, Inc., pp. 167–181.

M. E. Patarroyo et al., "Introduction of protective immunity against experimental infection with malaria using synthetic peptides", *Nature*, vol. 328, Aug. 1987, pp. 629–632.

E. Riley, "Malaria vaccine trials: SPf66 and all that", Current Biology, Ltd, ISSN 0952–7915, 1995, pp. 612–616.

G. S. Seetharamaiah et al., "Regulation of thyrotropin receptor protein expression in insect cells", *Journal of Molecular Endocrinology* (1999) 23, pp. 315–323.

W. A. Siddiqui et al., "Induction of Protective Immunity to Monoclonal–Antibody–Defined *Plasmodium falciparum* Antigens Requires Strong Adjuvant in Aotus Monkeys", *Infection and Immunity*, Apr. 1986, vol. 52, No. 1, pp. 314–318.

W. A. Siddiqui, "An Effective Immunization of Experimental Monkeys Against a Human Malaria Parasite, *Plasmodium falciparum*", *Science*, vol. 197, Mar. 1997, pp. 388–389.

W. A. Siddiqui et al., "Merozoite surface coat precursor protein completely protects Aotus monkeys against *Plasmodium falciparum* malaria", *Proc. natl. Acad. Sci. USA*, 84, 1987, pp. 3014–3018.

Garraud et al., "Immune responses to *Plasmodium falciparum*–merozoite surface protein 1 (MSP1) antigen, II. Induction of parasite–specific immunoglobulin G in unsensitized human B cells after in vitro T–cell priming MSP1$_{19}$", Immunology, 1997, pp. 497–505.

Holm et al., "Characterization of C–terminal merozoite surface protein–1 baculovirus recombinant proteins from *Plasmodium vivax* and *Plasmodium cynomolgi* as recognized by the natural anti–parasite immune response", Mol. and Biochem. Parasitology, 89, 1997, pp. 313–319.

Longacre et al., "*Plasmodium vivax* merozoite surface protein 1 C–terminal recombinant proteins in baculovirus", Mol. and Biochem. Parasitology, 64, 1994, pp. 191–205.

Perera et al., Baculovirus Merozoite Surface Protein 1 C–Terminal Recombinant Antigens are Highly Protective . . . ), Inspection and Immunity, 4/98. pp. 1500–1506.

* cited by examiner

```
      -70          -60         -50               -30         -20         -10
       |            |           |  * polh mRNA 5´end →|        |           |
      TAACCATCTCGCAAATAAATAAGTATTTTACTGTTTTCGTAACAGTTTTGTAATAAAAAAACCTA -4                                                   +736
       |         SstI      EcoRI      EcoRV      AatI       |
      TAgatctaagagctcccgggaattccatggatatctagataggcctTAA
        BglII            SmaI       NcoI       XbaI
```

6219
*Nhe*I
GCTAGCATC.ATG.AAA.TTC.TTA.GTC.AAC.GTT.GCC.CTT.GTT.TTT.ATG.GTC.GTG.TAC.
          M   K   F   L   V   N   V   A   L   V   F   M   V   V   Y

*Sma*I
ATT.TCT.TAC.ATC.TAT.GCG.GAC.CCA.AGC.CCC.ATG.GCA.ATA.TCT.GTC.ACA......
 I   S   Y   I   Y   A   D   P   S   P

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
gcaactgcaa gggcctcaat c                                           21

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
ccattagata gtccagccat cg                                          22

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
gcccatggaa ttcttagtca acgttgcc                                    28

<210> SEQ ID NO 4
<211> LENGTH: 27
<212> TYPE: DNA
<213> ORGANISM: Artificial Sequence
<220> FEATURE:
<223> OTHER INFORMATION: primer -continued

```
<400> SEQUENCE: 4
cctctagatt aggaactgca gaaaata                                              27

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5
taggcccccg ggatgaaatt cttagtcaac gttgcc                                    36

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
taggcccctc tagattagga actgcagaaa ata                                       33

<210> SEQ ID NO 7
<211> LENGTH: 49
<212> TYPE: DNA
<213> ORGANISM: Artificial Sequence
<220> FEATURE:
<223> OTHER INFORMATION: primer

<400> SEQUENCE: 7
atgcaccacc accaccacca cgcaatatct gtcacaatgg ataatatcc                      49

<210> SEQ ID NO 8
<211> LENGTH: 375
<212> TYPE: PRT
<213> ORGANISM: Unknown
<220> FEATURE:
<223> OTHER INFORMATION: amino acid sequence of PfMSP-1 42

<400> SEQUENCE: 8

Met Ala Ile Ser Val Thr Met Asp Asn Ile Leu Ser Gly Phe Glu Asn
  1               5                  10                  15

Glu Tyr Asp Val Ile Tyr Leu Lys Pro Leu Ala Gly Val Tyr Arg Ser
                 20                  25                  30

Leu Lys Lys Gln Ile Glu Lys Asn Ile Phe Thr Phe Asn Leu Asn Leu
             35                  40                  45

Asn Asp Ile Leu Asn Ser Arg Leu Lys Lys Arg Lys Tyr Phe Leu Asp
 50                  55                  60

Val Leu Glu Ser Asp Leu Met Gln Phe Lys His Ile Ser Ser Asn Glu
 65                  70                  75                  80

Tyr Ile Ile Glu Asp Ser Phe Lys Leu Leu Asn Ser Glu Gln Lys Asn
                 85                  90                  95

Thr Leu Leu Lys Ser Tyr Lys Tyr Ile Lys Glu Ser Val Glu Asn Asp
            100                 105                 110

Ile Lys Phe Ala Gln Glu Gly Ile Ser Tyr Tyr Glu Lys Val Leu Ala
            115                 120                 125

Lys Tyr Lys Asp Asp Leu Glu Ser Ile Lys Lys Val Ile Lys Glu Glu
        130                 135                 140

Lys Glu Lys Phe Pro Ser Ser Pro Pro Thr Thr Pro Pro Ser Pro Ala
145                 150                 155                 160
```

```
Lys Thr Asp Glu Gln Lys Lys Glu Ser Lys Phe Leu Pro Phe Leu Thr
                165                 170                 175
Asn Ile Glu Thr Leu Tyr Asn Asn Leu Val Asn Lys Ile Asp Asp Tyr
            180                 185                 190
Leu Ile Asn Leu Lys Ala Lys Ile Asn Asp Cys Asn Val Glu Lys Asp
        195                 200                 205
Glu Ala His Val Lys Ile Thr Lys Leu Ser Asp Leu Lys Ala Ile Asp
    210                 215                 220
Asp Lys Ile Asp Leu Phe Lys Asn Pro Tyr Asp Phe Glu Ala Ile Lys
225                 230                 235                 240
Lys Leu Ile Asn Asp Asp Thr Lys Lys Asp Met Leu Gly Lys Leu Leu
                245                 250                 255
Ser Thr Gly Leu Val Gln Asn Phe Pro Asn Thr Ile Ile Ser Lys Leu
            260                 265                 270
Ile Glu Gly Lys Phe Gln Asp Met Leu Asn Ile Ser Gln His Gln Cys
        275                 280                 285
Val Lys Lys Gln Cys Pro Glu Asn Ser Gly Cys Phe Arg His Leu Asp
    290                 295                 300
Glu Arg Glu Glu Cys Lys Cys Leu Leu Asn Tyr Lys Gln Glu Gly Asp
305                 310                 315                 320
Lys Cys Val Glu Asn Pro Asn Pro Thr Cys Asn Glu Asn Asn Gly Gly
                325                 330                 335
Cys Asp Ala Asp Ala Thr Cys Thr Glu Glu Asp Ser Gly Ser Ser Arg
            340                 345                 350
Lys Lys Ile Thr Cys Glu Cys Thr Lys Pro Asp Ser Tyr Pro Leu Phe
        355                 360                 365
Asp Gly Ile Phe Cys Ser Ser
    370                 375

<210> SEQ ID NO 9
<211> LENGTH: 1128
<212> TYPE: DNA
<213> ORGANISM: Unknown
<220> FEATURE:
<223> OTHER INFORMATION: Nucleotide sequence of PfMSP-142 3D7 Isolate

<400> SEQUENCE: 9
atggcaatat ctgtcacaat ggataatatc ctctcaggat ttgaaaatga atatgatgtt      60
atatatttaa aacctttagc tggagtatat agaagcttaa aaaacaaat tgaaaaaaac      120 attttacat ttaatttaaa tttgaacgat atcttaaatt cacgtcttaa gaacgaaaa      180 tatttcttag atgtattaga atctgattta atgcaattta acatatatc ctcaaatgaa      240 tacattattg aagattcatt taaattattg aattcagaac aaaaaaacac acttttaaaa      300
agttacaaat atataaaaga atcagtagaa atgatatta aatttgcaca ggaaggtata      360
agttattatg aaaaggtttt agcgaaatat aaggatgatt tagaatcaat taaaaaagtt      420
atcaaagaag aaaaggagaa gttcccatca tcaccaccaa caaacacctcc gtcaccagca      480 aaaacagacg aacaaaagaa ggaaagtaag ttccttccat ttttaacaaa cattgagacc      540
ttatacaata acttagttaa taaaattgac gattacttaa ttaacttaaa ggcaaagatt      600
aacgattgta atgttgaaaa agatgaagca catgttaaaa taactaaact tagtgattta      660
aaagcaattg atgacaaaat agatcttttt aaaaaccctt acgacttcga agcaattaaa      720
aaattgataa atgatgatac gaaaaaagat atgcttggca aattacttag tacaggatta      780
```

```
gttcaaaatt ttcctaatac aataatatca aaattaattg aaggaaaatt ccaagatatg      840
ttaaacattt cacaacacca atgcgtaaaa aaacaatgtc cagaaaattc tggatgtttc      900
agacatttag atgaaagaga agaatgtaaa tgtttattaa attacaaaca agaaggtgat      960
aaatgtgttg aaaatccaaa tcctacttgt aacgaaaata atggtggatg tgatgcagat     1020
gccacatgta ccgaagaaga ttcaggtagc agcagaaaga aaatcacatg tgaatgtact     1080
aaacctgatt cttatccact tttcgatggt attttctgca gttcctaa                 1128
```

<210> SEQ ID NO 10
<211> LENGTH: 11
<212> TYPE: PRT
<213> ORGANISM: Plasmodium falciparum

<400> SEQUENCE: 10

```
Thr Cys Thr Glu Glu Asp Ser Gly Ser Ser Arg
 1               5                  10
```

<210> SEQ ID NO 11
<211> LENGTH: 11
<212> TYPE: PRT
<213> ORGANISM: Plasmodium falciparum

<400> SEQUENCE: 11

```
Lys Cys Thr Glu Glu Asp Ser Gly Ser Asn Gly
 1               5                  10
```

MALARIA IMMUNOGENIC COMPOSITION

CROSS-REFERENCE TO RELATED APPLICATIONS

This application claims the benefit under 35 U.S.C. §119 (e) of U.S. provisional patent application No. 60/165,178 filed Nov. 12, 1999, U.S. provisional patent application No. 60/168,327 filed Dec. 1, 1999, and U.S. provisional patent application No. 60/226,861 filed Aug. 22, 2000, each of which are hereby incorporated by reference in their entirety.

TECHNICAL FIELD

This invention is in the field of biology. In particular, this invention relates to the cloning and expression of the C-terminal 42 kDa fragment of the Major Merozoite Surface Protein 1 ($MSP1_{42}$) or antigenic fragments thereof in a silkworm baculovirus expression system, the purification of the $MSP1_{42}$ and the production of a vaccine therefrom.

BACKGROUND OF THE INVENTION

Malaria is caused by protozoal parasites of the genus Plasmodium. There are four species that infect man, *P. falciparum P, vivax, P. malariae and P. ovale*. Of these *P. falciparum* is largely responsible for acute and often fatal malaria, but there is significant morbidity associated with each malaria infection and a large proportion of the world's population is at risk from the disease. It has been estimated that malaria is a public health problem in areas where 40% of the world's population live and the disease has severe social and economic consequences for these communities. There has been a recent resurgence of the disease due to the abandonment or breakdown of control measures and to an increasing resistance of the vector to insecticides and falciparum malaria to chemotherapy.

Thus, there is an urgent need to develop a vaccine effective against malaria.

SUMMARY OF THE INVENTION

In order to meet these needs, the present invention is directed to the use of a baculovirus expression system to produce a recombinant C terminal 42 kDa fragment of the Major Merozoite Surface Protein ($MSP1_{42}$) for use in a malaria vaccine. The expression system of the invention is silkworms infected with recombinant nuclear polyhedrosis virus (NPV). The silkworms are preferably *Bombyx mori* silkworms (BmNPV). The malaria vaccine finds use in treating and preventing malaria including malaria resulting from the four species of the protozoal parasites of the genus Plasmodium that infect humans: *P. falciparum P, vivax, P. malariae* and *P. ovale*.

The present invention is further directed to a method of producing a malaria vaccine, comprising: (a) expressing an immunogenic fragment of MSP $1_{42}$ in a baculovirus expression system; (b) purifying the immunogenic fragment; and (c) formulating the immunogenic fragment in a malaria vaccine. In the method, the immunogenic fragment may include all or a portion of the MSP $1_{42}$ protein. The MSP $1_{42}$ protein may include a hexa-histidine tail.

In the method of purifying a malaria vaccine of the invention, the immunogenic fragment may be purified by chromatography or electrophoresis. The chromatography purification method may be ion exchange chromotogaphy, metal chelate affinity chromatography; molecular weight sieving, high pressure liquid chromatography, affinity chromatography or antibody affinity chromatography. The electrophoresis procedure may be agarose, acrylamide or isoelectric focusing electrophoresis.

In the method of producing a malaria vaccine of the invention the vaccine may include an adjuvant. The adjuvant may be selected from the group consisting of aluminum phosphate, aluminum hydroxide, saponin, Quil A, muramyl dipeptide, monophosphoryl lipid A muramyl tripeptide, cytokines, diphteriatoxoid, exotoxin A, granulocyte-macrophage colony stimulating factor and phospholipid conjugates. The adjuvant may further be selected from the group consisting of Adjumer™; PCPP salt; polyphophazene; polyidi(carboxylatophenoxyl)phosphazene; Adju-Phos; Aluminum phosphate gel; β-glucan; glucan; Gamma inulin/ alum composite adjuvant; aluminum hydroxide gel; alum; N,N-dioctadecyl-$N^1$, $N^1$-bis(2-hydroexyethyl) propanediamine; N-(2-Deoxy-2-L-leucylamino-β-D-glucopyranosyl)-N-octadecyldodecanoylamide; Calcitriol; 25-dihydroxyvitamin D3; 1,25-di(OH)$_2$D$_3$; 1,25-DHCC; 1α,25-dihdroxycholecalciferol; 9,10-seco(5Z,7E)-5,7,10 (19)-cholestatriene-1α,3β,25-triol; Block Copolymer P1205; Cytokine-containing Liposomes; Cytokine-containing Dehydration Rehydration Vesicles; Dimethyl dioctadecylammonium bromide; demethyl distearylammonium bromide; Dehydroepiandrosterone; 5-androsten-3β-ol-17-one; dehydroisoandrosterone; androstenolone; prasterone; transdehydroandrosterone; Dimyristoyl phosphatidyl choline; sn-3-phosphatidyl choline-1,2-dimyristoyl; 1,2-dimyristoyl-sn-3-phosphatidyl choline; Dimyristoyl pposphatidylglcerol; sn-3-phosphatidyl glycerol-1,2-dimyristoyl, sodium salt; 1,2-dimyritoyl-sn-3-phosphatidyl glycerol; Deoxycholic Acid Sodium Salt; Gamma Inulin; Interleukin-1β; IL-10; IL-1; human Interleukin 1β mature polypeptide Interferon-γ; Immunoliposomes Containing Antibodies to Costimulatory Molecules; ImmTher™; N-acetylglucosaminyl-N-acetyhnuramyl-L-Ala-D-isoGlu-L-Ala-Glycerol dipalmitate; Imiquimod; 1-(2-methypropyl)-IH-imidazo[4,5-c]quinolin-4-amine; GMDP; N-acetylglucosaminyl-(β1-4)-N-acetylmuramyl-L-alanyl-D-isoglutamine; Gerbu Adjuvant; Interleukin-2; IL-2; T-cell growth factor; aldesleukin (des-alanyl-1, serine-125 human interleukin 2); Proleukin®; Teceleukin®; Interleukin-7; IL-7; Interleukin-12; IL-12; natural killer cell stimulatory factor (NKSF); cytotoxic lymphocyte maturation factor (CLMF); ISCOM(s)™; Immune stimulating complexes; Iscoprep 7.0.3.™; Liposomes; Liposomes (L) containing protein or Th-Cell and/or B-cell peptides, or microbes with or without co-entrapped interleukin-2, BisHOP or DOTMA; Loxoribine; 7-allyl-8-oxoguanosine; LT-OA or LT Oral Adjuvant; *E. coli* labile enteroxtoxin protoxin; MONTANIDE ISA 720; metabolizable oil adjuvant; MPL™; 3-Q-dsacyl-4'-monophosphoryl lipid A; 3D-MLA; MF59; MTP-PE; N-acetyl-L-alanyl-D-isoglutaminyl-L-alanine-2-(1,2-dipalmitoyl-sn-glcero-3-(hydroxy-phosphoryloxy)) ethylamide, mono sodium salt; MTP-PE Liposomes; MTP-PE Antigen presenting liposomes; Murametide; Nac-Mur-L-Ala-D-Gln-OCH3; Murapalmitine; Nac-Mur-L-Thr-D-isoGln-sn-glycerol dipalmitoyl; D-Murapalmitine; Nac-Mur-D-Ala-D-isoGln-sn-glcerol dipalmitoyl; NAGO; Neuraminidase-galactose oxidase; Non-Ionic Surfactant Vesicles; NISV.; Pleuran; PLGA, PGA, and PLA; Homo-and co-polymers of lactic and glycolic acid; Lactide/glycolide polymers; poly-lactic-co-glycolide; Pluronic L121; Poloxamer 401; PMMA; Poly-methyl methacrylate; PODDS™; Proteinoid microspheres; Poly rA; Poly rU; Poly-adenylic acid-poly-uridylic acid complex; Polysorbate 80; Tween 80; Sorbitan mono-9-octadecenoate poly(oxy-1,2-ethanediyl) derivatives; Protein Cochleates; QS-21; Stimulon™ QS-21 Adjuvant; Rehydragel HPA; High Protein Adsobency Aluminum Hydroxide Gel; alum; Rehydragel LV; low viscosity alluminum hydroxide gel; alum; S-28463; 4-Amino-otec, -dimethyl-2-ethoxmethyl-1H-imidazo[4,5-c]quinoline-1-ethanol; SAF-1; Scalvo peptide; IL-1β 163–171 peptide; Span 85; Arlacel 85, sorbitan trioleate; Specol; Marcol 52 (mineral oil, paraffins, and cycloparaffins, chain length 13–22 C atoms) Span 85 (emulsifier, sorbitan trioleate) Tween 85 (emulsfier, polyoxyethylene-20-trioleate); Squalane; Spinacane; Robane®; 2,6,10,15,19,23-hexamethyltetracosane; Squalene; Spinacene; Supraene; 2,6,10,15,19,23-hexamethyl-2,6,10,14,18,22 tetracosahexaene; Stearyl Tyrosine; Octadecyl tyrosine hydrochloride; Theramide™; N-acetylglucosaminyl-N-acetylinuramyl-L-Ala-D-isoGlu-L-Ala-dipalmitoxy propylmadie (DTP-DPP); Threonyl-MDP; Termurtide™; [thr$^1$]-MDP ; N-acetyl muramyl-L-threonyl-D-isoglutamine; Ty Particles; and Ty-VLPs, (Virus Like Particles)

In the method of purifying a malaria vaccine of the invention the vaccine may include cholera toxin. The cholera toxin may be cholera toxin subunit A or cholera toxin subunit B.

The present invention is also directed to a method of immunizing a patient to malaria, comprising (a) preparing a malaria vaccine by expressing an immunogenic fragment of $MSP1_{42}$ in a baculovirus expression system; (b) purifying the immunogenic fragment; (c) formulating the immunogenic fragment in a malaria vaccine; and (d) administering the vaccine to said patient.

In the method of of immunizing a patient to malaria, the immunogenic fragment may be purified by chromatography or electrophoresis. The chromatography purification method may be ion exchange chromotogaphy, molecular weight sieving, high pressure liquid chromatography, affinity chromatography or antibody affinity chromatography. The electrophoresis procedure may be selected from agarose, acrylamide and isoelectric focusing electrophoresis.

In the method of immunizing a patient to malaria, the vaccine may include an adjuvant. In the method of immunizing a patient to malaria, the vaccine may include cholera toxin. The cholera toxin may be cholera toxin subunit A or cholera toxin subunit B.

The present invention is also directed to a malaria vaccine produced by the method of: (a) expressing an immunogenic fragment of $MSP1_{42}$ in a bacculovirus expression system; (b) purifying the immunogenic fragment; and (c) formulating the immunogenic fragment in a malaria vaccine.

The vaccine may further include an adjuvant. The vaccine may include cholera toxin. The cholera toxin may be cholera toxin subunit A or cholera toxin subunit B.

The present invention is further directed to a method of treating a patient with malaria, compromising: (a)expressing an immunogenic fragment of $MSP1_{42}$ in a baculovirus expression system; purifying the immunogenic fragment; (c) formulating the immunogenic fragment in a malaria vaccine; and (d) administering the malaria vaccine to the patient.

In the method of treating a patient with a malaria vaccine the immunogenic fragment may be purified by chromatography or electrophoresis. The chromatography purification method may be ion exchange chromotogaphy, molecular weight sieving, high pressure liquid chromatography, affinity chromatography and antibody affinity chromatography. The electrophoresis procedure may be selected from agarose, acrylamide and isoelectric focusing electrophoresis.

In the method of treating a patient with a malaria vaccine of the invention the vaccine may include an adjuvant. In the method of treating a patient with a malaria vaccine of the invention the vaccine may include cholera toxin. The cholera toxin may be cholera toxin subunit A or cholera toxin subunit B.

The invention is further directed to a method of purifying an immunogenic fragment of $MSP1_{42}$, comprising: expressing the immunogenic fragment in a bacculovirus expression system wherein the baculovirus expression system is *Bombyx mori* silkworms infected with nuclear polyhedrosis virus and purifying the immunogenic fragment by chromatography or electrophoresis.

In the method purifying an immunogenic fragment of $MSP1_{42}$, the chromatography purification method may be selected from ion exchange chromotogaphy, molecular weight sieving, high pressure liquid chromatography, affinity chromatography and antibody affinity chromotography. and the electrophoresis procedure may be agarose, acrylamide or isoelectric focusing electrophoresis.

The present ivention is further directed to an isolated and purified immunogenic fragment of $MSP1_{42}$ purified by the methods of the invention.

The present invention is further directed to a silkworm capable of expressing recombinant MSP $1_{42}$. The silkworm may be *Bombyx mori* silkworm infected with recombinant nuclear polyhedrosis virus.

BRIEF DESCRIPTION OF THE DRAWINGS

The invention will be better understood by reference to the drawings, in which.

DETAILED DESCRIPTION OF THE INVENTION

DEFINITIONS

Figure 1:
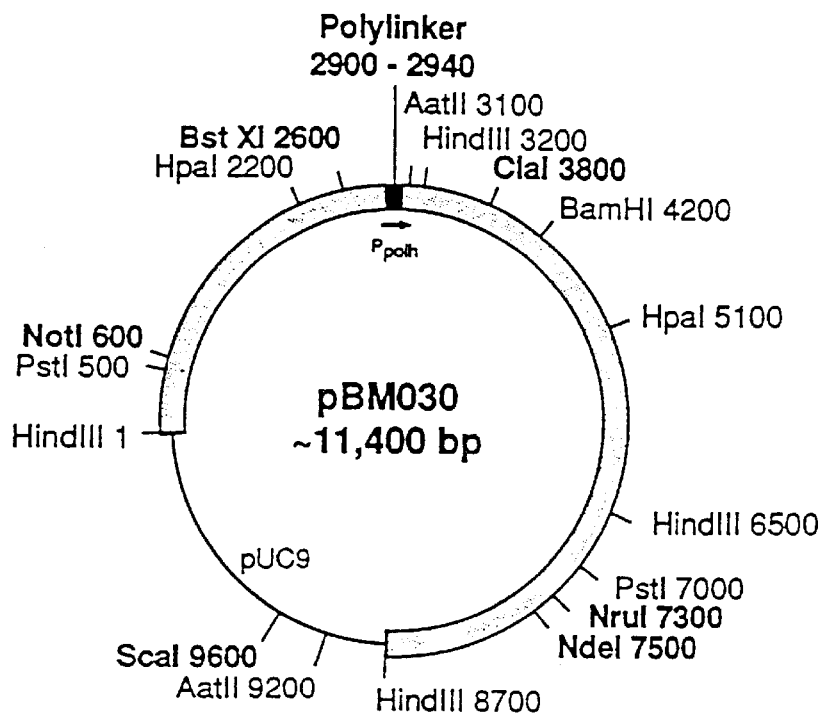
FIG. 1 shows a restriction map of transfer vector pBM030 (upper) and the flanking sequence of the multiple cloning site (lower).

To ensure a complete understanding of the invention, the following definitions are provided:

Malaria: Malaria is any group of diseases usually intermittent or remittent characterized by attacks of chills fever, and sweating caused by a parsitic protozoan which is transferred to the human bloodstream by a mosquito.

Major Merozoite Surface Protein 1 (MSP1): Major merozoite surface protein 1 (MSP1) is a surface protein of *Plasmodium falciparum* which is a parasite which causes malaria. The C-terminal 42 kDa fragment of *Plasmodium falciparum* $MSP1_{42}$ is also known as PfMSP-1$_{42}$. Pf MSP-1$_{42}$; MSP1-42 and PfMSP1-42 are synonymous. The $MSP1_{42}$ is a protein of approximately 195 kDa in size. The N-terminal region of PfMSP1–42 comprises of non-conserved (or dimorphic) amino acid sequences, and the C-terminal region of PfMSP1$_{42}$ comprises conserved sequences. The C-terminal conserved region of PfMSP1$_{42}$ (a 19 kDa fragment), is also known as MSP1-19. Limited variant-specific sequences are found at the C-terminal region of PSP1–42 (or MSP1-19) and these include the sequences EKNG, ETSR, and QKNG.

Malaria Vaccine: A malaria vaccine is a preparation used as a preventive innoculation against malaria or as a treatment for malaria including the malaria caused by the four species of the protozoal parasites of the genus Plasmodium that infect man, *P. falciparum P. vivax, P. malariae* and *P. ovale* The malaria vaccine of the present invention includes purified MSP1$_{42}$ or antigenic fragments thereof isolated from silkworms infected with a baculovirus vector containing all or part of the MSP1$_{42}$ sequence. The vaccine may further include adjuvants and/or various carriers as further described below.

Polypeptide: Polypeptide means any chain of amino acids, regardless of length or post-translational modification (e.g., glycosylation or phosphorylation).

Substantially Pure Polypeptide: Substantially pure polypeptide means a MSP1$_{42}$ polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight MSP1$_{42}$ polypeptide. A substantially pure MSP1$_{42}$ polypeptide may be obtained, for example, by extraction from a natural source (e.g., a plasmodium) by expression of a recombinant nucleic acid encoding a MSP1$_{42}$ polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include, without limitation, those derived from eukaryotic organisms but synthesized in *E. coli* or other prokaryotes, or those derived from a eukaryotic cell. which does not normally synthesize such a protein, or those derived from a eukaryotic cell engineered to overexpress such a protein.

Immunogenic Fragment: Immunogenic fragments are peptide fragments of a least 5–8 amino acids of a protein such as MSP 1$_{42}$ wherein the fragaments are capable of inducing an immune response in a mammal such as a human. The treated mammal mounts an immune response resulting in the production of antibodies against the MSP 1$_{42}$ immunogenic fragments of which circulate in the mammal's blood stream Recombinant Protein: A recombinant protein is a protein expressed in a non-native organism or cell. In the context of the present invention, recombinant MSP 1$_{42}$ is MSP1$_{42}$ expressed in a silkworm cell. Herein recombinant MSP1-42, recombinant MSP1$_{42}$ and Sp42 are synonymous.

Substantially Pure DNA: Substantially pure DNA means DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

Positioned for Expression: Positioned for expression means that the DNA molecule is positioned adjacent to a DNA sequence which directs transcription and translation of the sequence (i.e., facilitates the production of, e.g., a recombinant MSP1$_{42}$ polypeptide or RNA molecule).

Taking into account these definitions, the present invention is directed to a vaccine comprising purified MSP1$_{42}$. The MSP1$_{42}$ vaccine of the invention is produced by expressing MSP 1$_{42}$ in a baculovirus expression system in silkworms, purifying the MSP1$_{42}$ protein and preparing a vaccine containing the purified MSP1$_{42}$ 1. Baculovirus Expression System Baculoviruses are a diverse group of closed-circular double-stranded DNA viruses of the family Baculoviridae, which are found mostly in insects. The baculo portion of the name refers to the rod-shaped capsids of the virus particles. The Baculoviridae can be divided into two sub-families: the Eubaculovirinae (occluded baculoviruses) and the Nudibaculovirinae (non-occluded baculoviruses). The Eubaculovirinae produce crystalline proteinaceous structures called occlusion bodies, which are absent in the Nudibaculovirinae. The Eubaculovirinae subfamily is made up of two genera: granulosis viruses (GVs) and nuclear polyhedrosis viruses (NPVs). The virus used in the present invention, the *Bombyx mori* Nuclear Polyhedrosis Virus (BmNPV), is a NPV.

There are a number of advantages in using the *Bombyx mori* Nuclear Polyhedrosis Virus (BmNPV) baculovirus as an expression vector. Firstly, being eukaryotic origin, the insect cells can correctly fold and modify the expressed foreign proteins with their biological activities retained. Secondly, the double-stranded DNA genome of the virus can be easily manipulated by general molecular biology techniques and the rod-shaped viral capsid is rather "flexible" in accommodating large DNA insert. Thirdly, the recombinant baculoviruses cannot survive in the environment owing to the lack of protection by occlusion bodies, thus posing less biohazards. Fourth, in contrast to the Autographa californica Nuclear Polyhedrosis Virus (AcNPV) expression system which is limited to cell culture and is expensive, the BmNPV system used in the present invention can be adopted to produce recombinant proteins in silkworm larvae in large quantity and can be produced at a fraction of the cost of using cell culture. Fifth, BmNPV has a narrow host range and is therefore biologically safer to use. Because of these advantages, the BmNPV baculovirus expression system of the present invention is an ideal system for the expression of MSP-1$_{42}$ protein.

2. Cloning and Expression of MSP 1$_{42}$.

Insect cells are the preferred hosts for the baculovirus vectors of the invention. In the present invention, the preferred host is silkworm *Bombyx mori* cells.

The large size of the BmNPV genomic DNA (~130 kbp) makes it sensitive to minor mechanical damage such as shearing during pipetting. Because of this, direct insertion of PfMSP-1$_{42}$ DNA into the viral genome by conventional cloning techniques is not possible. In order to insert the PfMSP-1$_{42}$ DNA into BmNPV, an indirect cloning method was employed as detailed in the Examples below. The PCR product of PfMSP-1$_{42}$ was first cloned into a BmNPV-based transfer vector, pBM030, to generate the recombinant pBM030-PfMSP-1$_{42}$ transfer vector. Recombinant BmNPVs were then generated by cotransfecting BmN cells with the purified BmNPV genomic DNA and the recombinant transfer vector. By homologous recombination, the cloned PfMSP-1$_{42}$ DNA sequence was inserted into the viral genome. A total of three recombinant BmNPVs were produced by this method as described in the Examples below. Each of the recombinant BmNPVs carries a different form of PfMSP-1$_{42}$, namely a secretory form (the sp42 construct) with a honeybee melittin signal peptide, an intracellular form with a hexa-histidine tag fused to the N-terminal (the hp42 construct), and the original unmodified intracellular form (the p42 construct).

3. Purification of MSP $1_{42}$

Methods for purifying recombinant MSP $1_{42}$ are well known and can be generally divided into chromatographic methods, for example, ion exchange chromatography, molecular weight sieving, high pressure liquid chromatography, affinity chromatography, antibody affinity chromatography and electrophoretic methods, e.g., electrophoresis on agarose or acrylamide gels and isoelectric focusing. Any of these methods can be adapted to purify MSP $1_{42}$.

A preferred method of purifying MSP$1_{42}$ is immuno affinity chromatography. In immunoaffinity chromatography, an antibody to MSP $1_{42}$ is immobilized on a chromatographic substrate, a mixture containing MSP $1_{42}$ is applied to the substrate under conditions allowing the antibody to bind MSP $1_{42}$, the unbound material is removed by washing, and the bound MSP $1_{42}$ is eluted using, for example, high or low pH, protein denaturants or chaotropes.

For example, MSP $1_{42}$ may be purified by affinity chromatography using one or a combination of immobilized antibodies such as those described below covalently bound to agarose beads or bound non-covalently via a goat-anti mouse IgM antibody to Staphylococcus aureaus protein G beads. MSP $1_{42}$ isolation can also be achieved, for example, by incubating cell extracts with anti-MSP $1_{42}$ antibodies, described below, attached to a solid phase, such as chemical conjugation to agarose beads.

4. Vaccine Preparation

To prepare vaccines, purified MSP $1_{42}$ or immunogenic fragments of MSP $1_{42}$ are formulated and packaged using methods and materials known to those skilled in the art of vaccines, examples of which are described below. As used herein, an immunogenic fragment of a protein is a protein fragment of at least five to eight amino acids that elicits an immune response in an animal or individual.

a. Adjuvants

Adjuvants may, optionally, be employed and are preferred in some embodiments. Vaccines can be combined with an adjuvant, in an amount effective to enhance the immune response. Various adjuvants which find use in the invention include those described at http://www.niaid.nih.gov/aidsvaccine/pdf/compendium.pdf which is hereby incorporated by reference. In addition, a common adjuvant widely used in humans is alum, that is, aluminum phosphate or aluminum hydroxide. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, and phospholipid conjugates such as those described by Goodman-Snitkoff, et al., J. Immunol. 147: 410–415 (1991) which is hereby incorporated by reference, can also be used.

Further adjuvants include Adjumer™; PCPP salt; polyphophazene; polyidi(carboxylatophenoxy)lphosphazene; Adju-Phos; Aluminum phosphate gel; β-glucan; glucan; Gamma inulin/alum composite adjuvant; aluminum hydroxide gel; alum; N,N-dioctadecyl-$N^1$,$N^1$-bis(2-hydroexyethyl) propanediamine; N-(2-Deoxy-2-L-leucylamino-β-D-glucopyranosyl)-N-octadecyldodecanoylamide; Calcitriol; 25-dihydroxyvitamin D3; 1,25-di$(OH)_2D_3$; 1,25-DHCC; 1α, 25-dihdroxycholecalciferol; 9,10-seco(5Z,7E)-5,7,10 (19)-cholestatriene-1α,3β,25-triol; Block Copolymer P1205; Cytokine-containing Liposomes; Cytokine-containing Dehydration Rehydration Vesicles; Dimethyl dioctadecylammonium bromide; demethyl distearylammonium bromide; Dehydroepiandrosterone; 5-androsten-3β-o1-17-one; dehydroisoandrosterone; androstenolone; prasterone; transdehydroandrosterone; Dimyristoyl phosphatidyl choline; sn-3-phosphatidyl choline-1,2-dimyristoyl; 1,2-dimyristoyl-sn-3-phosphatidyl choline; Dimyristoyl pposphatidylglcerol; sn-3-phosphatidyl glycerol-1,2-dimyristoyl, sodium salt; 1,2-dimyritoyl-sn-3-phosphatidyl glycerol; Deoxycholic Acid Sodium Salt; Gamma Inulin; Interleukin-1β; IL-10; IL-1; human Interleukin 1β mature polypeptide Interferon-γ; Immunoliposomes Containing Antibodies to Costimulatory Molecules; ImmTher™; N-acetylglucosaminyl-N-acetyhnuramyl-L-Ala-D-isoGlu-L-Ala-Glycerol dipalmitate; Imiquimod; 1-(2-methypropyl)-1H-imidazo[4,5-c]quinolin-4-amine; GMDP; N-acetylglucosaminyl-(β1–4)-N-acetylmuramyl-L-alanyl-D-isoglutamine; Gerbu Adjuvant; Interleukin-2; IL-2; T-cell growth factor; aldesleukin (des-alanyl-1, serine-125 human interleukin 2); Proleukin®; Teceleukin®; Interleukin-7; IL-7; Interleukin-12; IL-12; natural killer cell stimulatory factor (NKSF); cytotoxic lymphocyte maturation factor (CLMF); ISCOM(s)™; Immune stimulating complexes; Iscoprep 7.0.3.™; Liposomes; Liposomes (L) containing protein or Th-Cell and/or B-cell peptides, or microbes with or without co-entrapped interleukin-2, BisHOP or DOTMA; Loxoribine; 7-allyl-8-oxoguanosine; LT-OA or LT Oral Adjuvant; *E. coli* labile enteroxtoxin protoxin; MONTANIDE ISA 720; metabolizable oil adjuvant; MPL™; 3-Q-dsacyl-4'-monophosphoryl lipid A; 3D-MLA; MF59; MTP-PE; N-acetyl-L-alanyl-D-isoglutaminyl-L-alanine-2-(1,2-dipalmitoyl-sn-glcero-3-(hydroxy-phosphoryloxy)) ethylamide, mono sodium salt; MTP-PE Liposomes; MTP-PE Antigen presenting liposomes; Murametide; Nac-Mur-L-Ala-D-Gln-OCH3; Murapalmitine; Nac-Mur-L-Thr-D-isoGln-sn-glycerol dipalmitoyl; D-Murapalmitine; Nac-Mur-D-Ala-D-isoGln-sn-glcerol dipalmitoyl; NAGO; Neuraminidase-galactose oxidase; Non-Ionic Surfactant Vesicles; NISV.; Pleuran; PLGA, PGA, and PLA; Homo-and co-polymers of lactic and glycolic acid; Lactide/glycolide polymers; poly-lactic-co-glycolide; Pluronic L121; Poloxamer 401; PMMA; Polymethyl methacrylate; PODDS™; Proteinoid microspheres; Poly rA; Poly rU; Poly-adenylic acid-poly-uridylic acid complex; Polysorbate 80; Tween 80; Sorbitan mono-9-octadecenoate poly(oxy-1,2-ethanediyl) derivatives; Protein Cochleates; QS-21; Stimulon™ QS-21 Adjuvant; Rehydragel HPA; High Protein Adsobency Aluminum Hydroxide Gel; alum; Rehydragel LV; low viscosity alluminum hydroxide gel; alum; S-28463; 4-Amino-otec,-dimethyl-2-ethoxmethyl-1H-imidazo[4,5-c]quinoline-1-ethanol; SAF-1; Scalvo peptide; IL-1β 163–171 peptide; Span 85; Arlacel 85, sorbitan trioleate; Specol; Marcol 52 (mineral oil, paraffins, and cycloparaffins, chain length 13–22 C atoms) Span 85 (emulsifier, sorbitan trioleate) Tween 85 (emulsfier, polyoxyethylene-20-trioleate); Squalane; Spinacane; Robane®; 2,6,10,15,19,23-hexamethyltetracosane; Squalene; Spinacene; Supraene; 2,6,10,15,19,23-hexamethyl-2,6,10,14,18,22 tetracosahexaene; Stearyl Tyrosine; Octadecyl tyrosine hydrochloride; Theramide™;

N-acetylglucosaminyl-N-acetylinuramyl-L-Ala-D-isoGlu-L-Ala-dipalmitoxy propylmadie (DTP-DPP); Threonyl-MDP; Termurtide™; [thr$^1$]-MDP;N-acetyl muramyl-L-threonyl-D-isoglutamine; Ty Particles; Ty-VLPs, (Virus Like Particles)

For oral administration, it is known that an admixture of trace amounts of cholera toxin (CT), either cholera toxin subunit A, cholera toxin subunit B, or both, and a second antigen stimulate a mucosal immunity to the co-administered antigen. Furthermore, there is a dramatic humoral immune response to the second antigen instead of the immune tolerance that is elicited by oral delivery of the antigen alone. Thus, mucosally delivered CT functions as a powerful immunostimulant or adjuvant of both mucosal and humoral immunity. It is therefore preferred to enhance immunogenicity of the orally administered antigen by including CT in the vaccine.

For parenteral administration, adjuvants include muramyl dipeptides, muramyl tripeptide, cytokines, diphtheria toxoid, and exotoxin A. Commercially available adjuvants include QS-21 from Cambridge Biosciences, Worcester, Mass., and monophosphoryl lipid A (MPLA) from Ribi Immunochem.

A group of growth factors termed colony stimulating factors which support survival, clorial expansion, and differentiation of hematopoietic progenitor cells are also useful as adjuvants. Granulocyte-macrophage colony stimulating factor (GM-CSF) belongs to this group and induces partially committed progenitor cells to divide and differentiate in the granulocyte-macrophage pathways.

The commercially available GM-CSF from the Immunex Corporation is provided as a sterile, white, preservative-free, lyophilized powder and is intended for intravenous infusion following reconstitution with 1 ml sterile water for injection, USP and is know as LEUKINE. The pH of the reconstituted, isotonic solution is 7.4.+−.0.3. When used as an adjuvant, LEUKINE may be reconstituted with sterile water or MSP1$_{42}$ with the vaccine preparation of this invention. If reconstituted with water then LEUKINE is administered by intramuscular injection at the same site as immunization with the MSP1$_{42}$ vaccine or is first mixed with the MSP1$_{42}$ vaccine preparation. The vaccine/GM-CSF mixture obtained by either reconstituting the GM-CSF with the MSP1$_{42}$ vaccine preparation directly or by mixing the water reconstituted GM-CSF with the MSP1$_{42}$ vaccine is then administered by intramuscular, subcutaneous or intradermal injection.

b. Carriers

Numerous carriers for administration of MSP 1$_{42}$ vaccine compounds are known. These include, but are not limited to, simple liquid carriers, and polymeric and lipid compositions. Simple liquid carriers, such as water or a buffered saline, can be used, either alone or in combination with other carriers.

The carrier may also be a polymeric delayed-release system. Synthetic polymers are particularly useful in the formulation of a vaccine to effect the controlled release of antigens. An example of this is described by Kreuter, Microcapsules and Nanoparticles in Medicine and Pharmacology, pages 125–148 (M. Donbrow, ed., CRC Press) which is incorporated herein by reference. The use of other particles have demonstrated that the adjuvant effect of these polymers depends on particle size and hydrophobicity.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters, and polyamides, particularly those that are biodegradable.

A frequent choice of a carrier for pharmaceuticals and more recently for antigens is poly (d,1-lactide-co-glyco-lide) (PLGA). This is a biodegradable polyester that has a long history of medical use in erodible sutures, bone plates and other temporary prostheses, where it has exhibited no toxicity. A wide variety of pharmaceuticals including peptides and antigens have been formulated into PLGA microcapsules. A body of data has accumulated on the adaptation of PLGA for the controlled release of antigen, for example, as reviewed by Eldridge et al., Current Topics in Microbiology and Immunology 146: 59–66 (1989) which is hereby incorporated by reference. The PLGA microencapsulation process uses a phase separation of a water-in-oil emulsion. In this process, the MSP 1$_{42}$ vaccine is prepared as an aqueous solution and the PLGA is dissolved in a suitable organic solvent such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Proteosomes, combinations of protein and liposomes, can also be used as carriers for combination vaccines, using the MSP 1$_{42}$ as the protein component. The procedures and materials for the use of proteosomes are as described in Lowell et al., Science 240: 800 (1988); Lowell, in New Generation Vaccines (Woodrow and Levine, eds., Marcel Dekker, N.Y., 1990), Ch. 12, pages 141–160; and Orr et al., Infect. Immun. 61: 2390 (1993) which are hereby incorporated by reference.

It will be understood by those skilled in the art that the immunogenic MSP 1$_{42}$ vaccine composition can contain other physiologically acceptable ingredients such as water, saline or a mineral oil such as Drakeol™, Markol™, and squalene, to form an emulsion, or in combination with aqueous buffers, or encapsulated within a capsule or enteric coating to protect the protein from degradation while passing through the stomach.

5. Vaccine Administration

In a preferred embodiment, the MSP 1$_{42}$ vaccine is packaged in a single dosage for immunization by parenteral, that is, intramuscular, intradermal or subcutaneous, administration; or nasopharyngeal, that is, intranasal, administration. The effective dosage is determined using standard techniques, such as antibody titer. The antigen may be lyophilized for resuspension at the time of administration or in solution. If administered with adjuvant, the adjuvant may be administered in combination with or in the vicinity of the MSP 1$_{42}$ vaccine.

Immunity is measured using assays to detect and quantitate antibodies that bind to the MSP 1$_{42}$. Cellular immunity is measured using assays that measure specific T-cell responses such as delayed type hypersensitivity (DTH) and lymphocyte proliferation. The dosage is determined by the antigen loading and by standard techniques for determining dosage and schedules for administration for each antigen, based on titer of antibody elicited by the antigen administration. As used herein, a dose effective to elicit an immune response is considered to be one that causes antibody titer to increase compared to untreated animals or individuals, using any of the known methods of titering antibodies.

Circulating antibodies to recombinant MSP $1_{42}$ are detected by enzyme immunoassay using recombinant MSP $1_{42}$ as antigen. Such assays are described in. detail in the Examples below.

The following examples are presented by way of illustration, not of limitation.

EXAMPLES

General

1. Reagents for Bacterial Culture

Luria-Bertani (LB) medium was prepared by dissolving 10 g bacto-tryptone (Difco, Detroit, Mich.), 5 g bacto-yeast extract (USB, Cleveland Ohio), and 10 g NaCl in 1 L $dH_2O$. The medium was autoclaved for 20 minutes at 121° C. and 1.1 $kg/cm^2$ on liquid cycle before use.

Ampicillin (Ap) solution was purchased from USB (Cleveland, Ohio) and 50 mg/mL stock solution in $dH_2O$ was prepared. The stock solution was sterilized by filtration through a 0.2 µm pore-size membrane filter (Schleicher & Schuell GmbH, Dassel, Germany). One-millilitre aliquots were made and were stored at –20° C.

LBAp medium was sterile LB medium supplemented with Ap at 100 µg/mL medium. LB and LBAp agar plates were prepared as follows. LB agar medium was prepared by the addition of agar (Sigma, St. Louis, Mo.) to LB medium to 1.5% (w/v) before autoclaving. For LBAp agar medium, Ap was supplemented at 100 µg/mL agar medium after autoclaving. Luke-warm agar medium was poured into 90 mm disposable petri dishes at ~20 ml/dish. The agar plates were allowed to set and stored at room temperature.

SOB medium was prepared as follows. A solution of 2% (w/v) bacto-tryptone, 0.5% (w/v) bacto-yeast extract, 10 mM NaCl, and 2.5 mM KCl was prepared and sterilized by autoclaving. Afterward, 0.2 µm pore-size membrane filter-sterilized $MgCl_2$ and $MgSO_4$ mix (1M each) was supplemented to a final concentration of 10 mM each to constitute the SOB medium.

SOB and SOBAp agar plates were prepared in the same way as LB and LBAp agar plates. SOB and SOBAp agar stabs were prepared as follows. SOB agar medium was SOB medium supplemented with agar to 0.8% (w/v). For SOBAp agar medium, Ap was supplemented at 100 µg/mL SOB agar medium after autoclaving. Three millilitres of the medium was aliquoted into each autoclaved glass vials with screw-on caps fitted with rubber gaskets. The stabs were allowed to set at room temperature at a 45° inclination. After incubating at 37° C. for 24 hours to check for contamination, the agar stabs were stored in the dark at room temperature until use.

SOC medium was SOB medium supplemented with 20 mM glucose solution sterilized by 0.2 µm pore-size membrane filtration. RF1 solution consisted of 100 mM RbCl, 50 mM $MnCl_2.4H_2O$, 30 mM potassium acetate, 10 mM $CaCl_2.2H_2O$, and 15% (w/v) ultrapure glycerol (USB, Cleveland, Ohio). The final pH was adjusted to 5.80 with acetic acid. The solution was sterilized by 0.2 µm pore-size membrane filtration.

RF2 solution consisted of 10 mM (3-[N-Morpholino] propanesulfonic acid), sodium salt (MOPS), 10 mM RbCl, 75 mM $CaCl_2.2H_2O$, and 15% (w/v) ultrapure glycerol. The final pH was adjusted to 6.80 with 5M NaOH. The solution was sterilized by 0.2 µm pore-size membrane filtration.

2. Reagents for Miniprep of Plasmid DNA

Solution I consisted of 50 mM glucose, 25 mM Tris-HCl at pH8.0 and 10 mM EDTA. The solution was autoclaved before use. It was stored at 4° C. Solution II was prepared by dissolving 1% (w/v) SDS in 0.2M NaOH solution. Solution III consisted of 60 mL 5M potassium acetate solution and 11.5 mL glacial acetic acid and was made up to 100 mL with sterile $dH_2O$. TE buffer was a solution of 10 mM Tris-HCl at pH8.0 and 1 mM EDTA. The buffer was autoclaved before use.

3. Reagents for Plasmid DNA Preparation

The following reagents were used within the Qiagen® plasmid midi kit to isolate plasmid DNA. Buffer P1 consisted of 50 mM Tris-HCl at pH8.0, 10 mM EDTA and 100 µg/mL of RNase A. The buffer was stored at 4° C. after the addition of RNaseA. Buffer P2 consisted of 200 mM NaOH and 1% SDS. Buffer P3 was 3M potassium acetate at pH5.5. Buffer QBT consisted of 750 mM NaCl, 50 mM MOPS at pH7.0, 15% of ethanol and 0.15% Triton X-100. Buffer QC consisted of 1M NaCl, 50 mM MOPS at pH7.0 and 15% of ethanol. Buffer QF consisted of 1.25M NaCl, 50 mM Tris-HCl at pH8.5 and 15% of ethanol.

4. Reagents for Agarose Gel Electrophoresis

Tris-acetate-EDTA (TAE) electrophoresis buffer was prepared as follows. A 50× stock solution was prepared by dissolving 242 g Tris base in 800 mL $ddH_2O$. Afterward, 100 mL 0.5M EDTA solution (pH8.0) and 57.1 mL glacial acetic acid were added. The solution was made up to 1 L with $ddH_2O$. It was diluted 50-fold before use. Tris-borate-EDTA (TBE) electrophoresis buffer was prepared as follows. A 10× stock solution was prepared by dissolving 108 g Tris base, 55 g boric acid in 800 mL $ddH_2O$. Forty millilitres of 0.5M EDTA solution, pH8.0, were added. The solution was made up to 1L with $ddH_2O$ and was diluted 10-fold before use.

DNA sample loading buffer was prepared as follows. A 6×buffer was prepared by mixing 0.25% (w/v) bromophenol blue, 0.25% (w/v) xylene cyanol FF and 40% (w/v) sucrose solution in sterile $dH_2O$. The buffer was stored at 4° C.

5. Reagents for DNA Sequencing

40% acrylamide mix consisted of 38% (w/v) acrylamide (USB, Cleveland, Ohio) plus 2% (w/v) bis-acrylamide (bis) (Bio-Rad, Hercules, Calif.) in $ddH_2O$. The 40% acrylamide mix was filtered through a 0.45 µm pore size membrane filter (Schleicher & Schuell) before use. The filtered solution was stored at 4° C. in a dark bottle.

DNA sequencing gel mix was prepared as follows. For every 100 mL of 6% DNA sequencing gel mix, a solution of 15 mL 40% acrylamide mix, 50 g urea and 10 mL 10×TBE buffer was freshly prepared. The volume was made up to 100 mL with $ddH_2O$. The gel mix was then filtered through Whatman® 3MM Chr chromatography paper. Four hundred microlitres 10% (w/v) ammonium persulphate solution and 25 µL TEMED (BioRad, Hercules, Calif.) were added and the gel mix was immediately casted into a 21×50 cm Sequi-Gen GT Sequencing Cell (Bio-Rad) by injection. Sequenase reaction buffer was a solution consisting of 200 mM Tris-HCl at pH7.5, 100 mM $MgCl_2$ and 250 mM NaCl. ddA, ddT, ddG and ddC termination mixes were prepared as follows. Each tube of termination mix consisted of 80 µM each of dATP, dTTP, dGTP and dCTP together with 50 mM NaCl and 8 µM of the respective dideoxy-ribonucleoside triphosphates. The labeling mix was a 5× concentrated solution of 7.5 µM each of dGTP, dCTP, and dTTP.

Diluted T7 DNA polymerase was prepared by mixing 1 µL Sequenase™ Version 2.0 T7 DNA polymerase, 0.5 µL Inorganic Pyrophosphatase, and 6.5 µL Enzyme Dilution Buffer (10 mM Tris-HCl, pH7.5, 5 mM DTT and 0.5 mg/mL BSA). 2× stop solution was composed of 95% formamide, 20 mM EDTA, 0.05% bromophenol blue and 0.05% xylene cyanol FF.

6. Reagents for Southern Hybridization

Denaturation solution consisted of 1.5M NaCl and 0.5M NaOH. The solution was autoclaved before use. Neutralization solution consisted of 1.5M NaCl in 1M Tris-HCl buffer at pH7.5. The solution was autoclaved before use. SET solution was prepared as follows. A 20× stock solution was prepared consisting of 3M NaCl, 20 mM EDTA and 0.4M Tris-HCl, pH7.8. The stock solution was autoclaved and it was diluted 5-fold before use. STE buffer consisted of 100 mM NaCl, 20 mM Tris-HCl, pH7.5 and 10 mM EDTA. The buffer was autoclaved before use. ExpressHyb hybridization solution was purchased from Clontech (Palo Alto, Calif.) in a package size of 500 mL/bottle. The solution was stored at room temperature and was pre-warmed at 60° C. to dissolve the precipitates before use. SSC buffer was prepared was prepared as a 20× stock solution. The 20× stock solution consisted of 3M NaCl and 0.3M sodium citrate, pH7.0. It was autoclaved before use. Wash Solution 1 was prepared by dissolving SDS in 2×SSC buffer to 0.05% (w/v). Wash Solution 2 was prepared by dissolving SDS in 0.1 ×SSC buffer to 0.1% (w/v).

7. Reagents for Insect Cell Culture and Virus Work

Grace's insect cell culture medium was purchased from GibcoBRL (Grand Island, N.Y.) in liquid form in a package size of 500 mL/bottle. The medium was supplemented with 500 mg/L $CaCl_2$, 2800 mg/L KCl, 3330 mg/L lactalbumin hydrolysate, 3330 mg/L yeastolate and L-glutamine. The medium was stored at 4° C.

Fetal bovine serum (FBS) was purchased from GibcoBRL (Grand Island, N.Y.) in a package size of 500 mL/bottle. Just before use, the serum was heat-inactivated (HIFBS) at 56° C. for 30 minutes. Aliquots of 20 mL were prepared and stored at −20° C. Antibiotic-antimycotic (100×) was also purchased from GibcoBRL (Grand Island, N.Y.) in liquid form in a package size of 100 mL/bottle. It contained 10,000 units of penicillin G, 10,000 $\mu$g streptomycin sulphate and 2,500 $\mu$g amphotericin B (Fungazone®) in 0.85% saline. Five-millilitre aliquots of this antibiotic-antimycotic (PSF) were made and stored at −20° C. before use.

Complete insect cell culturing medium was prepared by supplementing Grace's insect cell culture medium with 1% (v/v) PSF and 10% (v/v) HIFBS.

Infection medium was prepared by supplementing Grace's insect cell culture medium with 1% (v/v) PSF and 1% (v/v) HIFBS. Recovery culture medium was Grace's insect cell culture medium supplemented with 20% (v/v) HIFBS. Agarose solution was prepared as follows. A 2.5% (w/v) low temperature, low EEO sulphate content SeaKem® LE agarose solution (FMC® BioProducts, Santa Rosa, Calif.) was first prepared in $ddH_2O$ and autoclaved. It was melted in a microwave oven before use.

Agarose overlay medium was prepared as follows. The melted agarose solution and the complete insect cell culture medium were separately warmed in a 50° C. water bath. Just before overlaying onto infected BmN cells, 1 mL of the agarose solution and 3 mL of the complete insect cell culturing medium were mixed thoroughly in a sterile 5 mL snap-capped tube to constitute the agarose overlay medium.

Neutral red-agarose overlay medium was prepared as follows. Four millilitres of Neutral-red solution at 3.3 g/L (Sigma, St. Louis, Mo.) was premixed with 6 mL 2.5% SeaKem® LE agarose solution. The mixture was melted before use. One millilitre of the mixture was added to 3 mL pre-warmed complete insect cell culture medium to constitute the Neutral red-agarose overlay medium.

Occlusion body lysis buffer consisted of 0.1M $NaCO_3$ and 0.05M NaCl. It was autoclaved before use. DTT solution was prepared as follows. A 250 mM stock solution of dithiothreitol (DTT) was prepared by dissolving 0.7725 g DTT in 20 mL 0.01M sodium acetate solution, pH5.5. The DTT solution was sterilized by 0.2 $\mu$m pore-size membrane filtration. One-millilitre aliquots were prepared and kept at −20° C. PBS for insect cell culture was prepared by dissolving 8 g NaCl, 0.2 g KCl, 1.44 g $Na_2HPO_4$ and 0.24 g $KH_2PO_4$ in a final volume of 1 L $dH_2O$. The pH of the buffer was adjusted to 7.4 with 1M HCl and it was autoclaved before use.

8. RPMI-1640 Medium for Hybridoma Cell Line MAb5.2

Pre-packed RPMI-1640 powder with L-glutamine and 25 mM HEPES buffer (GibcoBRL, Grand Island, N.Y.) was dissolved in 1 L $ddH_2O$ containing 2 g $NaHCO_3$. The pH of the medium was adjusted to 7.4 and the medium was sterilized by 0.2 $\mu$m pore-size membrane filtration. Complete RPMI-1640 medium for MAb5.2 cell line was supplemented with 1% (v/v) PSF and 10% (v/v) HIFBS.

9. Reagents for SDS-PAGE

Solutions for making gels were prepared according to Sambrook, et al. (1989). For a 30% acrylamide mix, a working solution of 29% (w/v) acrylamide plus 1% (w/v) bis in $ddH_2O$ was prepared. It was filtered through a 0.45 $\mu$m pore size membrane filter before use. The solution was stored at 4° C. in a dark bottle. Other reagents were prepared by dissolving the corresponding chemicals in $ddH_2O$.

Tris-glycine electrophoresis buffer was prepared as a 5× stock solution by dissolving 15.1 g Tris base and 94 g glycine in 900 ml $dH_2O$. Fifty millilitres 10% (w/v) SDS solution was added, and the volume was adjusted to 1 L with $dH_2O$. The stock solution was diluted 5-fold before use.

Sample loading buffer was prepared as a 2× working solution with 4% (w/v) SDS, 125 mM Tris-Cl (pH6.8), 30% (v/v) glycerol and 0.002% (w/v) bromophenol blue. For reducing disulphide bonds of proteins, 5–10% (v/v) β-mercaptoethanol (Sigma, St. Louis, Mo.) was added just before use.

SDS-PAGE staining solution was prepared by dissolving 0.25 g Coomassie Brilliant Blue R-250 (Sigma, St. Louis, Mo.) in 90 mL 1:1 (v/v) methanol: $dH_2O$ mixture and 10 mL glacial acetic acid. SDS-PAGE destaining solution was prepared by mixing 250 mL ethanol with 80 mL glacial acetic acid and made up to 1 L with $dH_2O$. Silver stain fixative enhancer solution was prepared according to the instructions of the Silver Stain Plus Kit (Bio-Rad, Hercules, Calif.). It consisted of 10% (v/v) fixative enhancer concentrate (provided by the kit), 50% (v/v) reagent grade methanol and 10% (v/v) reagent grade glacial acetic acid in $ddH_2O$.

Silver stain staining substrate solution was prepared according to the instructions of the Silver Stain Plus Kit (Bio-Rad, Hercules, Calif.). Just before use, 1.5 mL each of the silver complex solution, reduction moderator solution, and image development reagent (all provided by the kit) were mixed and made up to 25 mL with. $ddH_2O$ (Solution 1). On the other hand, a 4% (w/v) development accelerator solution (Solution 2) was also freshly prepared by dissolving the development accelerator powder (provided by the kit) in $ddH_2O$. The two solutions were mixed together to constitute the staining substrate solution.

10. Reagents for Western Blotting

Bjerrum and Schafer-Nielsen transfer buffer was prepared by dissolving 5.82 g Tris and 2.93 g glycine in a minimal volume of $ddH_2O$. 3.75 mL 10% (w/v) SDS solution and 200 mL analytical grade absolute methanol were then added. The final volume was made up to 1 L with $ddH_2O$. The pH of the buffer ranged from 9.0 to 9.4.

PBS was prepared as a 5× stock solution by dissolving 40 g NaCl, 1 g KCl, 7.2 g $Na_2HPO_4$ and 1.2 g $KH_2PO_4$ in a final volume of 1 L dH$_2$O. The stock solution was diluted 5-fold with pH adjusted to 7.4 with HCl before use.

Wash buffer (PBST) was 1×PBS containing 0.05% (v/v) Tween® 20 (USB, Cleveland, Ohio). Blocking solution was PBST containing 5% (w/v) non-fat dried milk powder. AP substrate buffer was a buffer of 0.1M Tris, 0.1M NaCl and 5 mM MgCl$_2$. The pH of the buffer was adjusted to 9.5 with 1M HCl. AP substrate solution was prepared as follows. Nitro blue tetrazolium (NBT) solution was prepared by dissolving 10 mg (if tablet was used, one tablet of) NBT (Sigma, St. Louis, Mo.) in 1 mL ddH$_2$O. The solution was wrapped in tinfoil and kept at −20° C. 5-Bromo-4-chloro-3-indolyl phosphate (BCIP) solution was prepared by dissolving 50 mg BCIP (Sigma, St. Louis, Mo.) in 1 mL ddH$_2$O and kept at −20° C. Just before use, 300 μL NBT solution and 30 L BCIP solution were added to 10 mL AP substrate buffer (for each 7×5 cm$^2$ membrane) to constitute the AP substrate solution.

11. Reagents for ELISA

ELISA coupling buffer was prepared by dissolving 1.6 g Na$_2$CO$_3$ and 2.9 g NaHCO$_3$ in 1 L dH$_2$O. The pH of the solution was adjusted to 9.6 with 1M HCl.

Wash buffer was PBST. Blocking buffer (PBSTM) was PBST containing 3% (w/v) non-fat dried milk powder. Saturation buffer (PBS/BSA) was prepared by dissolving 1% (w/v) bovine serum albumin (BSA; Sigma, St. Louis, Mo.) in 1×PBS pH7.4. Secondary antibody buffer (PBST/BSA) was prepared by dissolving 1% (w/v) BSA in PBST. Horseradish peroxidase (HRP) substrate buffer was 100 mM trisodium citrate solution with pH adjusted to 4.1 with 1M HCl.

HRP substrate mix was prepared as follows. A 50×ABTS stock solution was prepared by dissolving 0.499 g 2,2'-azino-bis(3-ethylbenzthiazoline-6-sulfonic acid) diammonium salt (ABTS; Sigma, St. Louis, Mo.) in 20 mL HRP substrate buffer. One-millilitre aliquots were prepared and kept at −20° C. Just before use, one aliquot of ABTS was warmed at 37° C. For each millilitre of substrate solution, 200 μL 50×ABTS solution and 1.4 μL 30% (v/v) H$_2$O$_2$ were made up to 1 mL with HRP substrate buffer.

12. Reagents for RNA Experiments

Diethyl pyrocarbonate (DEPC)-treated ddH$_2$O was prepared by adding DEPC (Sigma, St. Louis, Mo.) to dH$_2$O to 0.1% (v/v). The DEPC-supplemented dH$_2$O was wrapped in tinfoil and stirred for 24 hours at room temperature. It was autoclaved before use.

RNA agarose gel electrophoresis buffer (MOPS buffer) was prepared as a 10× stock solution by dissolving 23.12 g (3-[N-Morpholino]propanesulfonic acid), sodium salt (MOPS), 2.05 g sodium acetate and 1.86 g EDTA in 1 L DEPC-treated dH$_2$O. The pH of the buffer was adjusted to pH7.0 and the buffer was sterilized by 0.2 μm pore-size membrane filtration before use.

RNA sample loading buffer was prepared by mixing 0.75 mL deionized formamide (BDH, Poole, England), 0.15 mL 10×MOPS buffer, 0.24 mL 37% formaldehyde (Riedel-de Haen, Seelze, Germany), 0.1 mL ultrapure glycerol, 80 μL 10% (w/v) of bromophenol blue and 0.1 mL DEPC-treated dH$_2$O. The buffer was dispensed into 200 μL aliquots and stored at −20° C. Each aliquot was supplemented with 10 g ethidium bromide (Bio-Rad, Hercules, Calif.) before use. 10×SSC was prepared by dissolving 87.65 g NaCl and 44.1 g sodium citrate in 1 L DEPC-treated dH$_2$O. The pH of the solution was adjusted to 7.0 with 5M NaOH. It was autoclaved before use.

13. Purification of PCR Products or Restricted DNA Fragments

PCR products or restricted DNA fragments were separated on TAE agarose gel stained with 10 μg ethidium bromide (EtBr) and visualized by UV trans-illumination (FotoDyne Inc.). Gel with the target DNA band was excised with a cutter and saved in a sterile 1.5 mL eppendorf tube. Three volumes (v/w) of 6M NaI were added, and the tube was immersed into a 55° C. water bath until the gel melted completely. The gel solution was incubated at room temperature for 5 minutes with occasional mixing after the addition of 10–20 μL EZ-Glassmilk® from the GeneClean® III Kit (Bio101, Inc., Vista, Calif.). The Glassmilk pellet was saved by centrifuging at 13,000 rpm at room temperature for 20 seconds. 0.5–1 mL ice-cold NEW Wash solution (see appendix 4) was added to wash the pellet. The tube was re-centrifuged at 13,000 rpm at room temperature for 20 seconds and the pellet was saved. The washing process was repeated twice. After removing the residual amount of NEW Wash solution, the Glassmilk pellet was resuspended in 10–20PL (as that of EZ-Glassmilk® added) Elution Solution™ provided by the kit. The supernatant was saved after centrifuging at 13,000 rpm at room temperature for 30 seconds. The elution process was repeated once and the supernatants were pooled. Purified DNA in the supernatant was examined by agarose gel electrophoresis.

14. Preparation of Competent E. coli for Transformation

E. coli strain DH5α or JM109 was streaked from agar stabs onto SOB agar plates the day before the preparation of competent E. coli cells. The streaked plates were incubated at 37° C. for 16–18 hours. Colonies of 2–3 mm in diameter were picked and inoculated into SOB medium at one colony per 10 mL medium in a sterile conical flask. The inoculum was shaken at 37° C. at 250 rpm until OD$_{600}$ reading reached 0.35–0.6. The bacterial suspension was transferred to a 50 mL Falcon tube and chilled on ice for 15 minutes. The bacteria were then harvested by centrifugation at 3,000 rpm at 4° C. for 15 minutes. RF1 solution was added to resuspend the bacterial pellet in a volume one-third of the original inoculum. The resuspended bacteria were kept on ice for 30 minutes and then centrifuged at 3,000 rpm at 4° C. for one hour. After discarding the supernatant, RF2 solution was added to resuspend the bacteria in a volume 1/12.5 of the original inoculum. After keeping on ice for 15 minutes, the bacteria were distributed into 200 μL-aliquots in pre-chilled sterile 1.5 mL eppendorf tubes. The competent E. coli cells were flash-frozen in liquid nitrogen and stored at −80° C.

15. Heat-shock Transformation of Plasmid DNA or Ligation Products Into Competent E. coli Cells Frozen competent E. coli cells were thawed on ice until the suspension was just liquefied. Plasmid DNA or ligation product to be transformed was added to each aliquot of competent cells in a volume of less than 20 μL. The tubes were finger-mixed gently and placed on ice for 60 minutes. Heat-shock transformation was performed by placing the tubes into a 42° C. water bath for 90 seconds and returning them immediately on ice for 2 minutes. 0.8 mL SOC medium was added to each tube. The transformed E. coli were recovered by incubating at 37° C. for 60 minutes with shaking at 250 rpm. The recovered cells were then spread onto LBAp agar plates and incubated at 37° C. for 16–18 hours. Bacterial colonies formed were picked and screened for the presence of recombinant plasmid by restriction mapping analysis.

16. Transformation of Ligation Products Into Electrocompetent E. coli.

One aliquot of ElectroMax™ DH10B E. coli (GibcoBRL, Gaithersburg, Md.) was thawed on ice, and 20 μL of it was transferred into a pre-chilled sterile 1.5 mL eppendorf tube.

The ligation product to be transformed was added to the E.coli cells and kept on ice for at least 15 minutes. A sterile disposable 2 mm gap Electroporation Cuvette Plus™ cuvette (BTX, Inc.) was also chilled on ice for at least 15 minutes. The cuvette, with the DNA-E. coli mixture, was placed into the pulse chamber of the EasyJect™ electroporator (EquiBio™). A single pulse at 2500V with impedance set at 25Ω was delivered for a period of less than five milliseconds. The electroporated cells were transferred to a sterile 1.5 mL eppendorf tube and allowed to recover in SOC medium as in the case of heat-shock transformation. Cells were spread onto LBAp agar plates and incubated at 37° C. for 16–18 hours. Bacterial colonies were picked and screened for the presence of recombinant plasmid by restriction mapping analysis.

17. MiniPrep of Plasmid DNA by Phenol-chloroform Extraction Method

Single colonies were first streaked onto a fresh LBAp agar plate as replica before inoculating into LBAp medium at 2 mL/colony. The replica plate was incubated at 37° C. for 16–18 hours, while the inocula were incubated at 37° C. for 16 cm –18 hours with shaking at 250 rpm. 1.5 mL of each bacterial suspension was harvested separately by centrifuging at 13,000 rpm at 4° C. for 90 seconds. Each bacterial pellet was resuspended in 100 µL ice-cold Solution I and kept on ice for five minutes. Two hundred microlitres freshly prepared Solution II at room temperature were then added. After mixing gently for 5 seconds, the bacterial lysate was kept on ice for 5 minutes. One hundred and fifty microlitres pre-chilled Solution III was added and the mixture was kept on ice for five minutes after vigorous vortexing. The neutralized lysate was centrifuged at 13,000 rpm at 4° C. for 10 minutes. The supernatant was saved in a sterile 1.5 mL eppendorf tube and an equal volume of phenol/chloroform was added. The mixture was mixed vigorously and centrifuged at 13,000 rpm at 4° C. for two minutes. The supernatant, with plasmid DNA extracted, was saved. Plasmid DNA was precipitated by adding one volume of absolute isopropanol at room temperature and centrifuging at 13,000 rpm at 4° C. for 30 minutes. The DNA pellet was saved and the residual amount of isopropanol was removed by freeze-drying in a SpeedVac (FTS Systems) for 15 minutes. The purified plasmid DNA was resuspended in 40 µL TE buffer with 10 µL RNase A (20 µg/mL) and incubated at 37° C. for three hours or 4° C. overnight to remove any RNA present.

18. Large-scale Preparation of Plasmid DNA

A single colony of bacteria was first streaked onto a fresh LBAmp agar plate as replica before inoculating into 25 mL LBAmp medium. The replica plate was incubated at 37° C. for 16–18 hours, while the inoculum was incubating at 37° C. for 16–18 hours with shaking at 250 rpm. Bacterial suspension was harvested by centrifuging at 8,000 rpm at 4° C. for five minutes. After resuspending in 4 mL Buffer P1, each bacterial pellet was added with 4 mL Buffer P2 and mixed gently. The bacterial lysate was incubated at room temperature for five minutes. Four millilitres ice-cold Buffer P3 was then added. The lysate was mixed gently and kept on ice for 15 minutes. The supernatant was saved by centrifuging the lysate at 13,000 rpm for 30 minutes at 4° C. Meanwhile, a Qiagen-tip 100 was equilibrated with 4 mL Buffer QBT by gravity flow. The supernatant saved was applied onto the Qiagen-tip 100, and the tip was washed twice with 10 mL Buffer QC by gravity flow. The bound plasmid DNA was eluted with 5 mL Buffer QF. The eluent was saved in a sterile 25 mL polypropylene centrifuge tube (Nalgene) and 0.7 volume of absolute isopropanol at room temperature was added. DNA precipitation was carried out by centrifugation at 13,000 rpm at 4° C. for 30 minutes. The plasmid DNA pellet was washed once with 2 mL 70% ethanol and re-centrifuged at 13,000 rpm at 4° C. for 15 minutes. After removing the residual amount of ethanol by freeze-drying, the purified plasmid DNA was resuspended in sterile TE buffer and stored at –20° C.

19. DNA Sequencing by T7 Sequenase™

Forward sequencing primer pBM-147 and reverse sequencing primer pBM+977 were custom-made by Gibco-BRL. The sequences of the two primers are as follows:

pBM-147: 5'GCA ACT GCA AGG GCC TCA ATC 3' SEQ ID NO:1 pBM+977: 5'CCA TTA GAT AGT CCA GCC ATC G 3' SEQ ID NO:2

The forward and reverse primers were designed to prime to position -147 upstream and +977 downstream of the initiation ATG codon of polh gene, respectively. Four micrograms of recombinant pBM030 plasmid with PfMSP-$1_{42}$ insert (200 ng/µL) was denatured at 37° C. for 30 minutes in the presence of 0.1 volumes of 2M NaOH and 2 mM EDTA. 0.1 volume of 3M sodium acetate, pH5.5, was added to neutralize the reaction mixture. Denatured plasmid was precipitated by keeping at –80° C. for 15 minutes in four volumes of absolute ethanol and harvested by centrifugation at 13,000 rpm at 4° C. for 10 minutes. The DNA pellet was washed with 70% ethanol and re-centrifuged at 13,000 rpm at 4° C. for 10 minutes. The DNA pellet was air-dried and dissolved in 7 µL sterile ddH$_2$O and 2 µL Sequenase reaction buffer. One microliter sequencing primer (0.5–1.0 pmol) was then added to the denatured plasmid DNA. Annealing reaction was carried out at 65° C. for two minutes followed by a gradual decrease of temperature to ambient over a period of 30 minutes. The annealing mixture was then chilled on ice. Four pieces of sterile 0.5 mL eppendorf tubes were separately labeled with A, G, C or T and loaded with 2.5 µL of the respective termination mix. The tubes were tightly capped and incubated at 37° C. in a PTC-100™ Programmable Thermal Controller (MJ Research, Inc.). The labeling mix was diluted 5-fold with sterile ddH$_2$O and kept on ice. One microliter 0.1M DTT, 2 µL diluted labeling mix, 0.5 µL Redivue [α-$^{35}$S]dATP from Amersham (10 µCi/µL; 1009 Ci/mmol) and 2 µL diluted T7 DNA polymerase were sequentially added into the annealing mixture. The total labeling mixture was kept at room temperature for five minutes. Finally, 3.5 µL of the total labeling mixture was quickly added to each termination tube (A, G, C and T) and mixed. The termination reaction was carried out at 37° C. for five minutes. The reaction was stopped by the addition of 4 µL 2× stop solution to each tube. The radioactively labeled DNA samples were denatured at 95° C. for five minutes and run on a 6% DNA sequencing gel casted in a 21×50 cm Sequi-Gen GT Sequencing Cell (Bio-Rad). The sequencing gel was vacuum-dried and exposed to BioMax MS films (Kodak) in a film cassette at room temperature for one to two days. The film was fixed and developed according to the manufacturer's instruction.

Example 1

Construction of pBM030/500NcoI Transfer Vector

1. Preparation of 500 bp NcoI Stuffer Fragment

Since the cloning sites employed (SmaI/XbaI or NcoI/XbaI) for cloning the PfMSP-$1_{42}$ (MSP $1_{42}$) insert are too close to each other, a stuffer fragment was first cloned into the NcoI site of pBM030 so that the successful double digestion of the transfer vector could be easily monitored (FIG. 1). The stuffer fragment was prepared by digesting ten micrograms of ppADH4fGH plasmid with 15 units of NcoI (Phannacia Biotech, USA) in 2×One-Phor-All Buffer Plus (OPA⁺ buffer). The reaction volume was adjusted to 40 µL by sterile ddH₂O in a 0.5 mL eppendorf tube. Restriction digestion was carried out at 37° C. overnight. A ~500 bp NcoI fragment was released and it was used as the stuffer fragment after purifying by GeneClean®.

2. Preparation of NcoI-restricted pBM030 Transfer Vector

The transfer vector pBM030 was a gift from Dr. Susumu Maeda of the Department of Entomology, University of California, Davis (FIG. 1). Seven micrograms of pBM030 was restricted with 20 units of NcoI in 2×OPA⁺ buffer. The reaction volume was adjusted to 40 µL by sterile ddH₂O. Restriction digestion was carried out at 37° C. overnight. The linearized pBM030 was purified by the GeneClean® method.

3. Cloning of 500 bp NcoI Stuffer Fragment Into pBM030

The ~500 bp NcoI stuffer fragment was ligated to NcoI-digested pBM030 with 0.5 unit of T4 DNA ligase (GibcoBRL) in a final reaction volume of 30 µL. Ligation was carried out at 16° C. for 18 hours. Twenty microlitres of the ligation mixture was transformed into competent *E. coli* strain DH5α by heat-shock transformation. The transformed DH5α cells were spread onto LBAp agar plates and incubated at 37° C. for 16–18 hours. Bacterial colonies established were picked for plasmid DNA purification. The "stuffed" transfer vectors were identified by restriction mapping analysis in which double digestion generated a 11.4 kb fragment corresponding to the linearized pBM030 vector and a 500 bp fragment corresponding to the stuffer fragment. The "stuffed" transfer vector was named pBM030/500NcoI.

Example 2

Construction of pBMO30-PiMSP-1$_{42}$ (Intracellular) Transfer Vector

1. Amplification of Intracellular-PfMSP-1$_{42}$ (p42) by Taq DNA Polymerase

Figure 2:
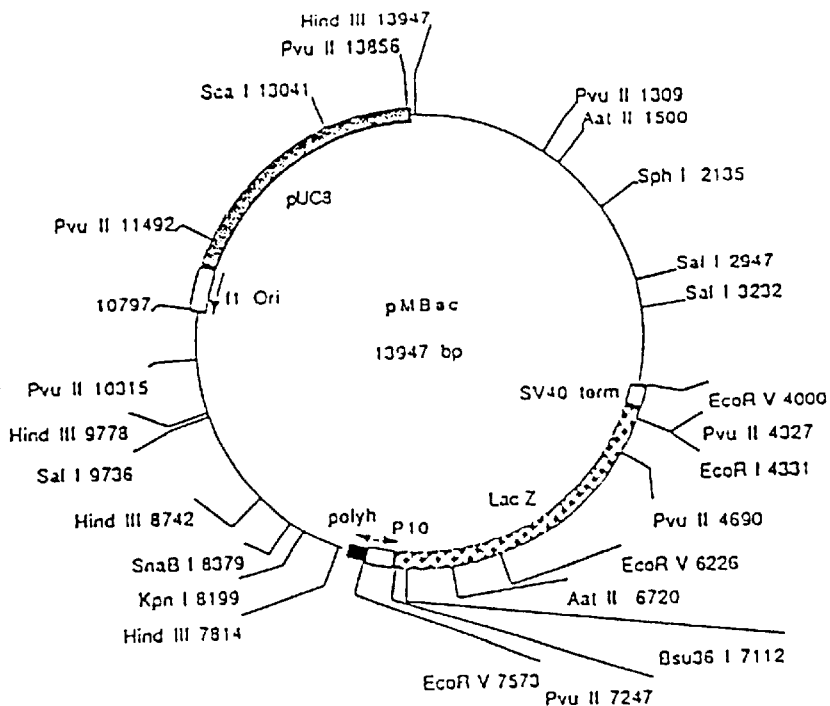
FIG. 2 shows a restriction map of transfer vector pMbac (upper) and the honeybee melittin signal peptide sequence downstream of the polh promoter (lower).
Figure 2:

The parent recombinant transfer vector pMbac-PfMSP-1$_{42}$ containing the PfMSP-1$_{42}$ insert was utilized (FIG. 2). A forward primer specific to the melittin signal peptide sequence of transfer vector pMbac (42k-F) and a reverse primer specific to the 3' end of PfMSP-1$_{42}$ insert (42k-R) were synthesized by Gene Assembler Special Oligonucleotide Synthesizer (Pharmcia LKB) with the following sequences:

42k-F: 5'GC<u>CCATGG</u>AATTCTTAGTCAACGTTGCC 3'-(SEQ ID NO:3)

42k-R: 5'CC<u>TCTAGA</u>TTAGGAACTGCAGAAAATA 3' (SEQ ID NO:4)

The A immediately downstream of the ATG in 42k-F was substituted by a G in order to insert a NcoI site (underlined) at the 5' end of the primer. Meanwhile, a XbaI site (underlined) was included in the reverse primer. This set of primers were originally designed to generate a secretory MSP1$_{42}$ construct by Polymerase Chain Reaction (PCR), in which the signal peptide sequence on pMbac would be co-amplified with the PfMSP-1$_{42}$ sequence. However, it was later found out that a NcoI site was introduced already into the junction of the 3' end of the signal peptide sequence and the 5' end of the MSP1$_{42}$ DNA on the parent vector pMbac-MSP1$_{42}$. As a result, the signal sequence of the resultant PCR product was removed after NcoI digestion. Fortunately, the unmodified form of the MSP1$_{42}$ sequence was generated after NcoI digestion and it could be cloned without frameshift into the transfer vector pBM030. Based on these observations, this set of primers was reserved for the generation of an intracellular construct of the MSP1$_{42}$. Another set of primers were subsequently designed to generate the secretory construct of the PfMSP-1$_{42}$ PCR was performed to amplify the MSP1$_{42}$ sequence using pMbac-PfMSP-1$_{42}$ as the template. For each reaction, 2 µL 2 mM dNTP, 5 µL 10×Taq PCR buffer, 3 µL each of forward and reverse primers (14.9 ng/µL and 15.3 ng/µL respectively), 1 µL pMbac-p42 (260 ng/µL) and 2.5 units of Taq DNA polymerase (Pharmacia Biotech, USA) were added and the reaction volume was made up to 50 µL with sterile ddH₂O. Amplification was carried out in a PTC-100™ Programmmable Thermal Controller (MJ Research, Inc.) with a five-minute incubation at 94° C. followed by 25 cycles of incubation as follows: 95° C. for 36 seconds, 55° C. for one minute, 72° C. for one minute. The reaction was stopped after a further incubation at 72° C. for ten minutes. The PCR product generated in this manner was named p42 and was purified by GeneClean®.

2. Subcloning of p42 Into pCRII Vector

Figure 3:
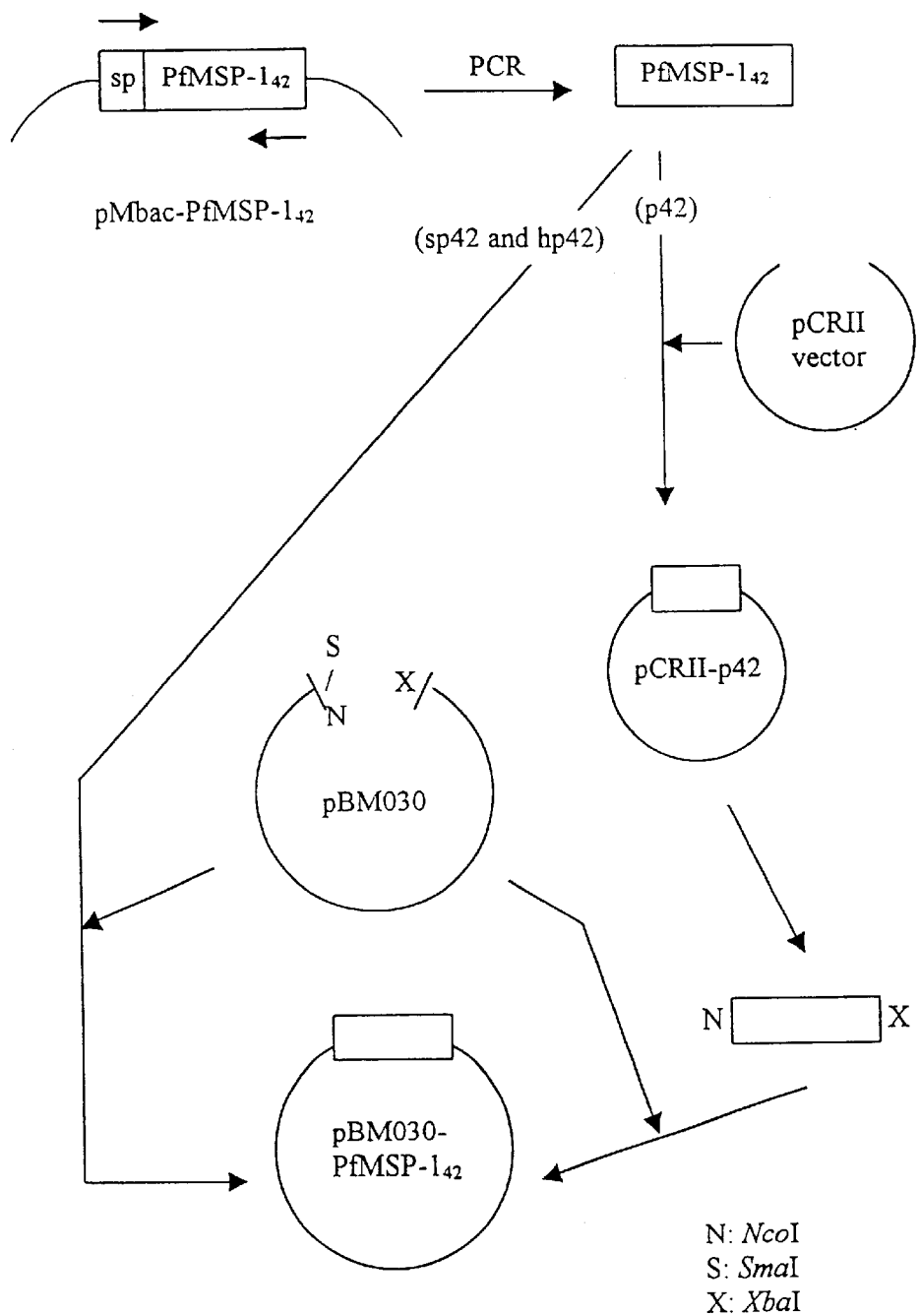
FIG. 3 shows the overall strategy in the construction of recombinant pBM030 transfer vector carrying PfMSP-1$_{42}$.

The purified p42 DNA was ligated to 25 ng of pCRII vector with two units of T4 DNA ligase in 1×ligation buffer (FIG. 3). Sterile ddH₂O was added to make up the volume to 20 µL. Ligation was carried out at room temperature for 48 hours. The ligation mixture was transformed into competent *E. coli* strain JM109 by heat-shock transformation. Transformants were spread onto LBAp agar plates with 2.5 µL 400 mM IPTG and 10 µL 2% (w/v) X-gal. The agar plates were incubated at 37° C. for 16–18 hours for blue colony formation. White colonies were picked to screen for recombinant plasmid by restriction mapping analysis. The successful recombinant plasmid obtained was named pCRII-p42.

3. Release of p42 From pCRII-p42

Fifteen micrograms of pCRII-p42 was first restricted at 37° C. overnight with 10 units of XbaI (Pharmacia Biotech, USA) in 1×OPA⁺buffer. Sterile ddH₂O was added to a final reaction volume of 80 µL. The XbaI was heat-inactivated at 65° C. for 20 minutes. Afterward, 10×OPA⁺buffer, 35 units of NcoI and sterile ddH₂O were added to start the NcoI restriction digestion according to the following equation:

$$V=0.2(F)-0.1(I)$$

V: volume of 10×OPA⁺ buffer required to increase the buffer strength from 1× to 2×

F: final volume of reaction mixture

I: initial volume of reaction mixture

The reaction mixture was further incubated at 37° C. for 5 hours. Restricted DNA fragments were resolved by agarose gel electrophoresis and the desired DNA band was purified by GeneClean®.

4. Restriction of pBM030/500NcoI for Cloning p42

12.5 µg of pBM030/500NcoI was digested with ten units of XbaI in a reaction volume of 80 µL. Restriction digestion was carried out at 37° C. for five hours. XbaI was heat-inactivated at 65° C. for 20 minutes. 10×OPA⁺ buffer and eight units of 20 NcoI were then added according to the equation mentioned before. NcoI digestion was carried out at 37° C. overnight. The double-digested pBM030 plasmid was purified by GeneClean®.

5. Cloning of p42 Into pBM030

The double-digested pBM030 was ligated with double-digested p42 in a mass ratio of at least 1:3. For each reaction, one unit of T4 DNA ligase was used in a reaction volume of 30 µL. Ligation was carried out at 16° C. for 24 hours. Two volumes of absolute ethanol were added to the reaction mixture and it was kept on ice for 15 minutes to precipitate the DNA. The ethanol was discarded after centrifuging at 13,000 rpm at 4° C. for 30 minutes. The DNA pellet was air-dried and resuspended in 20 μL TE buffer before electroporating into electrocompetent *E. coli* ElectroMax DH10B™ (GibcoBRL). The overall strategy in the cloning of PfMSP-1$_{42}$ into transfer vector pBM030 is summarized in FIG. 3.

Example 3

Construction of pBM030-PfMSP-1$_{42}$ (Secretory and 6×His-Tagged Intra-cellular) Transfer Vectors 1. Primers for Subcloning Secretory-PfMSP-1$_{42}$ (sp42) and 6×His Tagged Intracellular-PfMSP-1$_{42}$ (hp42)

Custom-made primers were ordered from GibcoBRL. For the construction of secretory-PfMSP-1$_{42}$ (sp42 construct), a new forward primer (42k-F-SmaIN) was designed with sequence specific to the honeybee melittin signal peptide sequence on the transfer vector pMbac. The sequence of 42k-F-SmaIN is as follows:

5' TAG GCC<u>CCC GGG</u>ATG AAA TTC TTA GTC AAC GTT GCC 3' (SEQ ID NO:5).

An end clamp of six nucleotides (TAGGCC) was introduced into the 5' position of the primer to facilitate docking of restriction enzyme onto the PCR product for digestion. A SmaI site (underlined) was included following the end clamp. A reverse primer (42k-R-XbaIN) was designed to prime to the 3' end of PfMSP-1$_{42}$ by the same strategy:

5'TAG GCC CC<u>T CTA GA</u>T TAG GAA CTG CAG AAA ATA 3' (SEQ ID NO:6)

A XbaI site (underlined) was included following the end clamp.

For the construction of 6×HisTagged Intracellular-PfMSP-1$_{42}$ (hp$^{42}$ construct), a forward primer (42k-F-6His) was designed to prime to the 5' end of PfNSP-1$_{42}$ as follows:

5'ATG CAC CAC CAC CAC CAC CAC GCA ATA TCT GTC ACA ATG GAT AAT ATCC 3' (SEQ ID NO:7)

Figure 4:
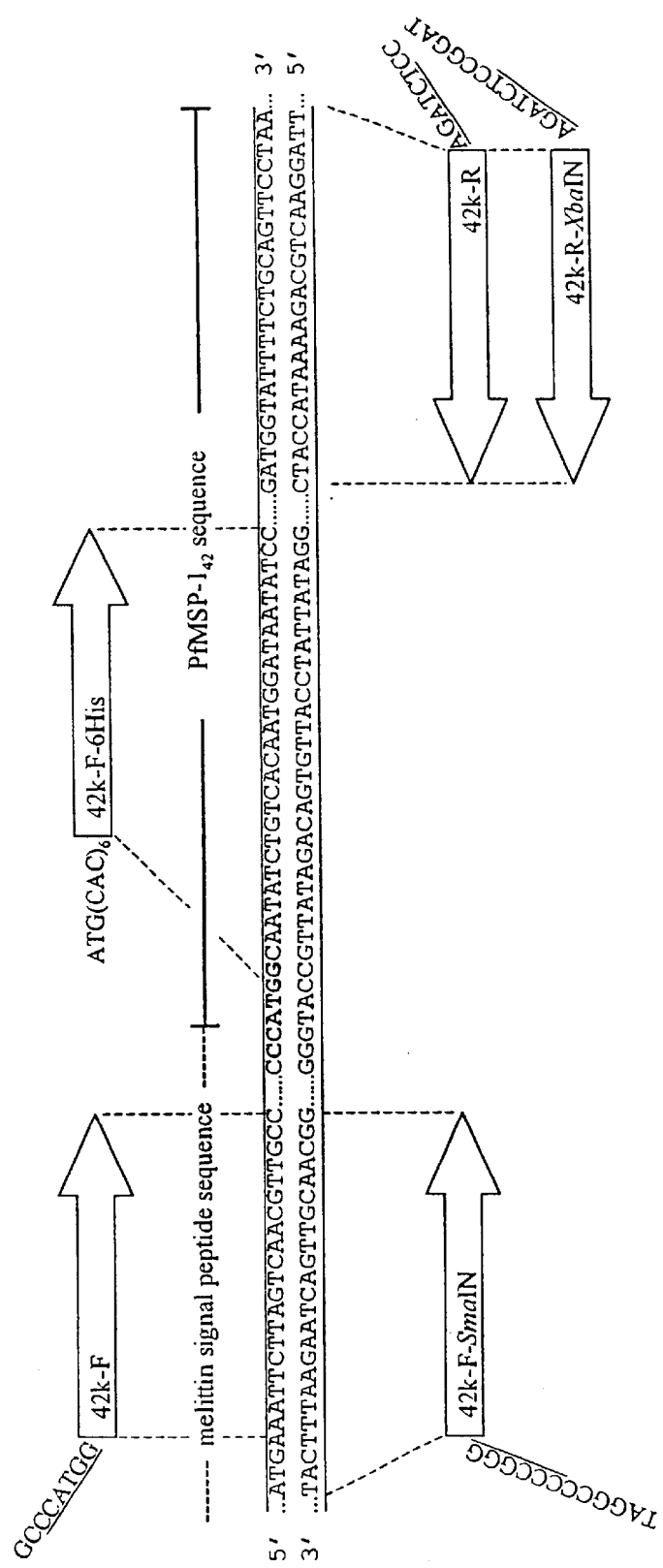
FIG. 4 shows the strategy of primer design in the construction of the different forms of recombinant PfMSP-1$_{42}$.

A start codon (ATG) was introduced together with a contiguous hexapeptide of histidine (underlined) to the 5' position of PfMSP-1$_{42}$. The reverse primer used was also 42k-R-XbaIN. The strategy used in primer design is illustrated in FIG. 4.

2. Amplification of MSP1$_{42}$ by Pfu DNA Polymerase

PCR was performed to amplify the sp42 and hp42 constructs using the two sets of primers mentioned above. The reactions were also carried out in a PTC-100™ Programmmable Thermal Controller (MJ Research, Inc.). For the sp42 construct, in each reaction, 5 μL 2 mM dNTP, 5 μL 10×Pfu PCR buffer, 2 μL each of forward and reverse primers (372.2 ng/μL and 267.5 ng/μL respectively), 1 μL pMbac-p42 (260 ng/μL) and 2.5 units of Pfu DNA polymerase (Stratagene) were added and it was made up to 50 μL with sterile ddH$_2$O. For the hp42 construct, volume of reagents used were the same except the primers: 1.5 μL for the forward and 2.5 μL for the reverse primer (634.6 ng/μL and 267.5 ng/μL respectively). PCR was started with a five-minute incubation at 94° C. followed by 25 cycles of incubation as follows: 95° C. for 36 seconds, 50° C. (for sp42 construct) or 55° C. (for hp42 construct) for one minute, 72° C. for three minutes. The reaction was stopped after a further incubation at 72° C. for ten minutes. The PCR products were purified by GeneClean®.

3. Restriction of PCR Products for Cloning Into pBM030 Transfer Vector

The PCR product of sp42 was digested with ten units each of SmaI and XbaI (Pharmacia Biotech) in 1×OPA$^+$ buffer in a reaction volume of 60 μL at 37° C. overnight. On the other hand, the PCR product of hp42 was digested only with ten units of XbaI in 1×OPA$^+$ buffer in a reaction volume of 20 μL at 37° C. overnight. The restricted sp42 and hp42 DNA was purified by GeneClean®.

4. Restriction of pBM030/500NcoI for Cloning of sp42 and hp42

7.5 μg of pBM030/500NcoI was restricted with ten units each of SmaI and XbaI in 1×OPA$^+$ buffer at 37° C. overnight. The reaction volume was made up to 30 μL with sterile ddH$_2$O. Double-digested pBM030 was purified by GeneClean®.

5. Cloning of sp42 and hp42 Into pBM030

Double-digested pBM030 was ligated with restricted sp42 or hp42 fragment in a mass ratio of 1:6. For each reaction, one unit of T4 DNA ligase (GibcoBRL) was used in 1×ligation buffer. Sterile ddH$_2$O was added to make up the reaction volume to 30 μL. Ligation was carried out at 16° C. for two days. Two volumes of absolute ethanol were added to the reaction mixture and it was kept on ice for 15 minutes to precipitate DNA. The ethanol was discarded after centrifuging at 13,000 rpm at 4° C. for 30 minutes. DNA pellet was air-dried and resuspended in 20 μL TE buffer before electroporating into electrocompetent *E. coli* ElectroMax DH10B™ (GibcoBRL).

The coding sequence of MSP1$_{42}$ is comprised of 375 amino acids. (stop codon excluded). The signal peptide at 5' of MSP1$_{42}$ consists of 25 amino acids =20. Cleavage of signal peptide left 4 amino acids. at the 5' of MSP1$_{42}$. As a result, the expressed sp42 protein has 379 amino acids. The complete amino acid sequence of PfmSP-1$_{42}$ is show in SEQ ID NO:8. The nucleotide sequence of pfmsp-1$_{42}$ 3D7 isolate is shown in SEQ ID NO:9.

Example 4

Virus Preparation

1. BmN Cells

The BmN cell line was originally derived from the pupal ovarian tissues of silkworms *Bombyx mori*. It was a gift from Dr. Susumu Maeda of the Department of Entomology, University of California, Davis. BmN cells were cultured in complete insect cell culture medium in 75 cm$^2$ culture flasks or 100 mm culture dishes (both from Coming®, Coming, N.Y.) at 27° C. Cells were subcultured by scraping them off with a sterilized rubber policeman every three days or before 100% confluence.

2. *Bombyx mori* Nuclear Polyhedrosis Virus (BmNPV)

Wild-type (wt) BmNPV (T3 isolate) was also a gift from Dr. Susumu Maeda of the Department of Entomology, University of California, Davis. The virus was propagated and amplified by in vitro infection of BmN cells. The culture medium of infected BmN cells was saved as viral stock and was stored at 4° C.

3. Rearing of Silkworms

Silkworms were provided by Dr. Z. Q. Meng of the Zhejiang Academy of Agricultural Sciences, Hangzhou. They were cultivated in spacious plastic trays at 27° C. and fed with fresh mulberry leaves or an artificial diet.

4. Infection of BmN Cells With Wild-type or Recombinant BmNPV

BmN cells growing in log phase (1–2×10$^6$ cells/mL) were seeded to culture dishes the day before infection (at 1.8×10$^6$ cells for each 60 mm dish and 5.5×10$^6$ cells for each 100 mm dish) and incubated at 27° C. overnight. Before infection, the complete insect cell culture medium was discarded and replaced with minimal volume of the infection medium. An appropriate volume of virus was inoculated. The infection process was carried out at room temperature for one hour with gentle and even rocking of the culture dishes at 15-minute interval. Three millilitres (for 60 mm dish) or 8 mL (for 100 mm dish) of complete insect cell culture medium was then added and the infected cells were further incubated at 27° C. until harvest.

5. Infection of Silkworms With Wild-type (wt) or Recombinant BmNPV and Extraction of Hemolymph Silkworms at early fifth instar (one to three days after molting, body weight between 2.5 to 4.0 g) were used for infection. Larvae were starved for three hours before viral infection. At the same time, wt or recombinant BmNPV was diluted ten-fold in Grace's insect cell culture medium supplemented with 1×PSF to $1.8 \times 10^4$ pfu/$\mu$L. Silkworms were anesthetized on ice for 20 minutes and then gently cleaned with 70% ethanol. Twenty microlitres of the diluted virus was injected longitudinally underneath the dorsal cuticle of each larva by a ½ c.c. Ultra-Fine® II short needle insulin syringe (Becton Dickinson). Infected silkworms were fed as usual at room temperature until symptoms of severe viral infection were observed (e.g. cessation of food consumption and movement, yellow cuticles, and softened body texture). To collect the hemolymph, prolegs of the silkworms were cut with scissors and hemolymph was squeezed into a sterile 1.5 mL eppendorf tube. Dithiothreitol (DTT) was immediately added to a final concentration of 5–10 mM to prevent melanization. The hemolymph was kept at 4° C. for occlusion body extraction or flash-frozen in liquid nitrogen and then stored at −80° C. for recombinant PfMSP-1$_{42}$ protein purification.

6. Isolation of Occlusion Bodies and Extraction of Wild-type BmNPV Particles

Ten millilitres of the wt BmNPV-infected hemolymph was centrifuged at room temperature at 3,500 rpm for ten minutes. The supernatant with oily debris was removed carefully. The pellet containing occlusion bodies was resuspended in 4 mL occlusion body lysis buffer. The lysis mixture was mixed gently and kept on ice for 30 minutes. After that, it was centrifuged at 3,500 rpm at room temperature for ten minutes. The supernatant with the released wt BmNPV particles was saved. The pellet was subjected to another round of lysis to extract virus particles from any unlysed occlusion bodies. The supernatants were pooled and stored at 4° C. for subsequent extraction of viral genomic DNA.

7. Purification of Wild-type BmNPV Genomic DNA

Two millilitres of the extracted BmNPV particles was layered onto 1 mL 40% (w/v) sucrose cushion in a 4.5 mL-polyallomer ultracentrifuge tube (Beckman) and centrifuged at 30,000 rpm at 15° C. for one hour. The viral pellet was saved and resuspended in 400 $\mu$L TE buffer. 0.05 volume of Proteinase K (Sigma, St. Louis, Mo.) at 20 mg/mL and 0.1 volume of 10% (w/v) SDS solution were added to lyse the viral coat proteins at 55° C. for one hour. One volume of phenol/chloroform was then added to extract the viral genomic DNA by mixing the content back-and-forth slowly for ten times. The mixture was centrifuged at 13,000 rpm at 4° C. for five minutes and the aqueous upper layer containing the viral DNA was saved. The extraction process was repeated twice with phenol/chloroform and two more times with chloroform alone. The organic layers were pooled and back-extracted by adding 100–200 $\mu$L TE buffer and re-centrifuged at 13,000 rpm at 4° C. for five minutes. The aqueous layers were pooled. The integrity of the purified viral DNA was checked by agarose gel electrophoresis. The DNA preparation was stored at 4° C.

8. Transfection of wt BmNPV Genomic DNA Into BmN Cells by Lipofusion

Two micrograms BmNPV DNA were made up to 300 $\mu$L with Grace's insect cell culture medium (solution A) just before transfection. Meanwhile, 30 $\mu$L of LipofectAMINE™ reagent (2 mg/ml) from GibcoBRL (Gaithersburg, Md.) were made up to 300 $\mu$L with Grace's insect cell culture medium (solution B), also just before transfection. Solution B was slowly added to solution A, and the mixture was incubated at room temperature for one hour to form a DNA-liposome complex. 2.4 mL Grace's insect cell culture medium was then slowly added to the DNA-liposome mixture. BmN cells in log phase were seeded to 60 mm dishes to 60% confluence the day before transfection; and they were washed twice with Grace's insect cell culture medium before the experiment. The DNA-liposome mixture was gently applied to the BmN cells, and transfection was allowed to proceed at 27° C. for 5 hours. Three millilitres of recovery culture medium (Grace's insect cell medium with 20% HIFBS) was added to stop the transfection process. The transfected BmN cells were further incubated at 27° C. for 19 hours. The medium was then replaced with 3 ml complete insect cell culture medium and incubated at 27° C. for six days. The success of the transfection process was confirmed by the presence of occlusion bodies.

9. Cotransfection of wt BmNPV Genomic DNA With Recombinant pBM030 Transfer Vector Into BmN Cells to Generate Recombinant BmNPV The procedure was the same as described for the transfection of wt BmNPV DNA, except 4 $\mu$g recombinant transfer vector were added to Solution A. On day 6, the culture medium was harvested with cell debris removed by centrifugation at room temperature at 3,500 rpm for ten minutes. This transfection stock was stored at 4° C. and used to generate the first progeny of the recombinant viral stock P1.

10. Viral Titer Determination

Serially diluted viral stock was used to infect BmN cells. After infection, the viral inoculum was aspirated and agarose medium was overlaid onto the cells. The agarose medium was allowed to set at room temperature for 20 minutes. Afterwards, the dishes were wrapped with parafilm (American National Can™) and incubated upside down at 27° C. for six days. On day 7, 1 mL Neutral red-agarose medium was overlaid onto the agarose medium and the cells were further incubated at 27° C. for 24 hours. The translucent viral plaques were visualized against a red-colored background and counted. Pfu was calculated according to the following equation: pfu/mL=number of plaques×(1/dilution factor)

Example 5

Purification of Recombinant BmNPV Carrying Different PfMSP-1$_{42}$ Constructs

1. Plaque Assay With Viral Plaque Lifting

The transfection stock serially diluted to $10^{-4}$–$10^{-6}$ fold in infection medium was used to infect BmN cells seeded in 60 mm dishes at $1.8 \times 10^6$ cells/dish. Mock-infected control was also performed. The volume of infection inoculum was 1 mL/dish. Agarose medium was overlaid onto the BmN cells. On day 6, the agarose overlays were gently pliered out and each of them was transferred to a larger sterile culture dish with the cell-side facing upward. A piece of autoclaved 0.45 $\mu$m pore-size ZetaProbe® membrane (Bio-Rad) cut to 60 mm in diameter was gently put onto each overlay. The membranes were allowed to soak for five minutes. A 23-G needle (Terumo) dipped in sterile black ink was used to pierce the membrane with the agarose overlay at three asymmetric positions. The membranes were then lifted with forceps and dried at room temperature for 20 minutes with the agarose-side up. The membranes were successively placed onto paper towels saturated with Denaturation solution and Neutralization solution, respectively, at room temperature for five minutes. Finally, the membranes were placed onto paper towels saturated with 4×SET buffer at room temperature for one minute. After air-drying for 15 minutes, a trace of recombinant pBM030 plasmid DNA was spotted on the edge of the mock-infected control membrane to act as a positive control. The membranes were sandwiched between stacks of Whatman® 3MM Chr chromatography paper and then placed between two glass-plates fastened with bulldog clips. The whole setup was then baked at 80° C. for two hours in a vacuum oven (Napco E series) to immobilize the DNA. The sandwich was then cooled down to room temperature and the membranes were then ready for Southern hybridization.

2. Southern hybridization: Synthesis of DNA probe by PCR

The PCR product of ip42 construct was used as the template for PfMSP-1$_{42}$-specific DNA probe synthesis. PCR and purification of PCR product were performed as described above. The purified ip42 DNA was diluted in TE buffer to a concentration of 25 ng/$\mu$L.

A. Radioactive Labelling of PfMSP-1$_{42}$ DNA Probe

One microliter of ip42 was mixed with 5 $\mu$L of the primer mix provided by the kit and made up to 50 $\mu$L with sterile ddH$_2$O. The DNA was denatured at 95° C. for five minutes and immediately chilled on ice. Ten microlitres labelling buffer and 5 $\mu$L Redivue [$\alpha$-$^{32}$P] dCTP from Amersham (10 mCi/mL, 3000 Ci/mmol) were subsequently added. Finally, 2 $\mu$L DNA polymerase I Klenow fragment (1 unit/$\mu$L) was added and the labeling mixture was incubated at 37° C. for ten minutes. The labeling reaction was stopped by the addition of 5 $\mu$L 0.2M EDTA. One microlitre of the labeling mixture was saved for monitoring of labeling efficiency (Tube 1).

B. Radioactive PfMSP-1$_{42}$ DNA Probe Purification

A NucTrap® column (Stratagene) was equilibrated with STE buffer by pushing 70 $\mu$L of the buffer through the column matrix with the syringe provided. The labeling mixture was applied and pushed through the column. The eluent was collected in a 1.5 mL eppendorf tube. Another 70 $\mu$L STE buffer was applied and the eluents were pooled. One microlitre of the pooled eluent (purified labeled PfMSP-1$_{42}$ DNA Probe) was saved in a separate 1.5 mL eppendorf tube as Tube 2 for monitoring of labeling efficiency. Radioactivity was detected by a Series-900Mini Monitor G-M tube (Mini-Instruments Ltd). When the radioactivity ratio of Tube 2 to 1 is below 20%, the whole 139 $\mu$L radioactive probe was used in hybridization reaction. The content of Tube 1 was added to 1 mL black ink and this radioactive ink was used as position markers in film exposure. The purified radioactive DNA probe was denatured at 95° C. for 5 minutes and chilled on ice before use.

C. Southern Hybridization

The hybridization buffer was pre-warmed to 60° C. in a water bath. Membranes containing the immobilized DNA were pre-hybridized in the hybridization buffer, Express Hyb™ hybridization buffer (clontech) (at 1 mL/5 cm$^2$ membrane) at 60° C. for 30 minutes with shaking. The hybridization buffer was replaced with fresh one and the denatured radioactive DNA probe was added. Hybridization was carried out at 60° C. for one hour with shaking. The hybridization mix was discarded and the membranes were washed in excess Wash Solution 1 at room temperature with several changes until the radioactivity decreased to a constant level. The membranes were then washed in excess Wash Solution 2 at 50° C. with several changes. When radioactivity was undetectable on the mock-infected control membrane, the membranes were blot-dried slightly. Each membrane was dotted with three asymmetric marks using the radioactive ink and was wrapped in plastic sheets. The presence of recombinant virus was detected by exposing the membranes to a BioMax MS film (Kodak) in a film cassette at −80° C. overnight. The film was fixed and developed according to the manufacturer's instruction.

3. Plaque Picking

Signals detected on the exposed film were used to locate the positions of recombinant viral plaques on the agarose overlays. A sterile P1000 pipette tip connected to a rubber bulb was used to penetrate the agarose to suck up the cell monolayer containing the recombinant plaque. Agarose plugs collected in this way were each resuspended in 200 $\mu$L infection medium at room temperature overnight to release the immobilized viruses. Fifty microlitres of the viral suspension were used to infect BmN cells for five days. The culture media collected at this stage were labeled as P1 recombinant viral stocks and they were used to perform further rounds of purification. The process of BmN cell infection, plaque assay, plaque lifting, and Southern hybridization was repeated two to three times in order to generate the final purified recombinant virus. The purified recombinant BmNPVs carrying p42, sp42 or hp42 construct of PfMSP-1$_{42}$ were named as BmNPV-p42, BmNPV-sp42 or BmNPV-hp42, respectively.

Example 6

Northern Hybridization

1. Extraction of Total RNA From Infected BmN Cells

Total RNA from infected BmN cells were isolated by TRIZOL® reagent (GibcoBRL, Grand Island, N.Y.) according to the manufacturer's instructions. The RNA contents were quantified by determining their optical density at 260 nm.

2. Immobilization of RNA Onto ZetaProbe® Membrane

The total RNA samples were resolved in RNA agarose gel electrophoresis under denaturing conditions. Afterward, the resolved RNA samples were transferred to a piece of ZetaProbe® membrane. The transfer process was carried out at room temperature overnight. After transfer, the membrane was rinsed with 2×SSC and air-dried briefly. RNA samples blotted onto the membrane were immobilized by two cycles of UV cross-linking at 120 mJ/cm$^2$ using a Spectrolinker™ XL-1000 UV crosslinker (Spectronics Corp.).

3. Northern Hybridization

The hybridization procedure was the same as in Southern hybridization, except the pre-hybridization and hybridization processes were carried out at 68° C.

Example 7

Expression of Recombinant PfMSP-1$_{42}$ Protein

1. In Vitro Expression in BmN Cell Culture 0.6×10$^6$ BmN cells in log phase were seeded to each well of a 6-well plate (Corning®, Corning, N.Y.) the day before infection. The cells were infected with recombinant BmNPV at a multiplicity of infection (MOI) of one and ten respectively. The infection process was performed as described above. Infected BmN cells and culture media were harvested separately daily until six days post-infection (d.p.i.). Each cell pellet was washed in PBS, pH6.2, lysed by sonication and lyophilization, and finally resuspended in 200 $\mu$L ddH$_2$O. Expression of recombinant PfMSP-1$_{42}$ protein was characterized by SDS-PAGE, Western blotting and sandwich ELISA in which a rabbit polyclonal anti-PfMSP-1$_{42}$ antiserum was used to probe the MAb5.2-captured recombinant PfMSP-1$_{42}$ protein.

2. In Vivo Expression in Silkworms

Silkworms were separately infected with the recombinant virus as described above. Hemolymph samples were harvested separately from three silkworms each day after infection for six or seven days. The expression of recombinant PfMSP-1$_{42}$ proteins was also characterized by sandwich ELISA, SDS-PAGE, and Western blotting.

Example 8

Protein Analysis

1. Protein Separation by Sodium Dodecylsulphate Polyacrylamide Gel Electrophoresis (SDS-PAGE)

SDS-PAGE was carried out according to Laemmli (1970). Resolving and stacking gels were prepared and casted in the Mini-PROTEAN® II electrophoresis cell (Bio-Rad). Each protein sample was mixed with an equal volume of 2×loading buffer and heated at 95° C. for five minutes. Samples were then centrifuged at room temperature at 13,000 rpm for five minutes. The clarified supernatants were loaded and the gels were run at 30 mA/gel.

2. Coomassie Brilliant Blue R-250 Staining of SDS Gels

Gels were stained in SDS-PAGE staining solution at room temperature overnight with gentle shaking. The gels were then destained in destaining solution at 55° C. with gentle shaking until the background was removed. After rinsing with tap water, the gels were dried under vacuum.

3. Silver Staining of SDS Gels by Silverstain

Each piece of resolving gel was fixed in 50 mL fixative enhancer solution for 20 minutes at room temperature with gentle shaking. The gel was then rinsed at room temperature for 20 minutes in 100 mL ddH$_2$O with three changes. Freshly prepared staining substrate solution (Silver Stain Plus Kit, Bio-Rad, CA) was added and the gel was stained at room temperature for about 15 minutes with gentle shaking. The gel was finally fixed in 50 mL 5% (v/v) glacial acetic acid at room temperature for 20 minutes and rinsed thoroughly in dH$_2$O before vacuum drying.

4. Protein Transfer Using Mini Trans-Blot Electrophoretic Transfer Cell

The process is also called "Wet Transfer". The resolving gel was equilibrated in chilled Bjerrum and Schafer-Nielsen transfer buffer for 15–30 minutes. A piece of 0.2 μm pore-size PVDF membrane (Bio-Rad, Hercules, Calif.) cut to the size of the gel was activated in reagent grade methanol and then equilibrated in transfer buffer for 15 minutes. A stack of Whatman® 3MM Chr Chromatography paper cut to the size of the gel was also soaked in the transfer buffer. The electrophoretic transfer cell was set up as illustrated in the instruction manual. Proteins were transferred from the gel to the PVDF membrane at 100V for one hour. After transfer, the membrane was ready for Western blotting. The efficiency of protein transfer was checked by staining the transferred gel with Coomassie Brilliant Blue R-250.

5. Western Blotting

Each membrane was blocked in 15 mL blocking buffer at room temperature for one hour. The blocking solution was changed and 20 μg of monoclonal antibody MAb5.2 was added. Probing of antigen was carried out at room temperature for one hour or at 4° C. overnight with gentle shaking. The membrane was then washed three times (ten minutes each) in 25 mL pre-chilled wash buffer. Afterward, 15 mL blocking buffer was added with 3 μL EIA-Grade affinity purified goat-anti-mouse IgG (H+L) AP conjugate (Bio-Rad, Hercules, Calif.). The membrane was incubated at room temperature with gentle shaking for one hour and it was washed again as mentioned before. Finally, after rinsing the membrane with 2 mL AP substrate buffer, the AP substrate solution was added. Color development was carried out in the dark at room temperature for 20 minutes and was stopped by flushing the membrane under tap water for two minutes. The membrane was then air-dried and kept away from strong light.

Example 9

Preparation of Monoclonal Antibody MAb5.2 by Raising Ascites in BALB/c Mice

1. Hybridoma Cell Line MAb5.2

MAb5.2 (IgG2$_b$) is specific for a disulphide-dependent conformational epitope on the carboxyl terminal of native PfMSP-1$_{42}$ protein. Siddiqui W. A. (1977) An Effective Immunization of Experimental Monkeys Against a Human Malaria Parasite, *Plasmodium falciparum*. Science 197: 388–9. The cells were grown in RPMI-1640 medium (GibcoBRL, Grand Island, N.Y.) supplemented with 1% (v/v) PSF and 10% (v/v) HIFBS at 37° C. with 5% CO$_2$.

2. Inoculation of BALB/c Mice With MAb5.2-secreting Cell

BALB/c mice were each primed with 0.5 mL Pristane (Sigma, St. Louis, Mo.) 7 to 14 days before inoculation. MAb5.2-secreting cells were harvested by trypsinization and centrifugation, washed twice in PBS, and adjusted to 5×10$^5$–5×10$^6$ cells in 0.5 mL PBS per dose. The mice were inoculated interperitoneally using a syringe with a 25-G needle. Ascites were harvested one to two weeks after inoculation, when sign of swelling at the abdominal region was observed.

3. Ascite Collection

Ascites were harvested by inserting a syringe with a 25-G needle at the peritoneal region. Blood cells were clotted at room temperature for one hour and ascites were then clarified by centrifuging at room temperature at 3,000 rpm for ten minutes. The supernatants were pooled and stored at −20° C.

4. Purification of MAb5.2 by Protein G Affinity Chromatography

All solutions used were first filtered through 0.45 μm pore-size membrane filters (Millipore) and chilled at 4° C. Frozen ascites were thawed at 4° C. overnight and then centrifuged at 9,000 rpm at 4° C. for 30 minutes. The supernatants were harvested carefully and diluted four times with PBS. The diluted ascites were gently stirred at 4° C. An equal volume of saturated ammonium sulphate solution was added drop-wise to the ascites to precipitate the immunoglobulins at 4° C. for 30 minutes. The mixture was then centrifuged at 9,000 rpm at 4° C. for 30 minutes. The supernatant was stored at 4° C. for monitoring purpose. On the other hand, the pellet was resuspended in four pellet-volumes of PBS and filtered through a 0.45 cm pore-size membrane filter unit. The filtrate was collected and 100 μL of it was saved as Test 1 (T1). The HiTrap™ Protein-G affinity Pharmacia Biotech (Uppsala, Sweden) column in storage mode was washed with three bed-volumes of dH$_2$O followed by three bed-volumes of PBS. A disposable 10 mL syringe, with plunger removed, was connected to the column and loaded with the crude immunoglobulin solution. The plunger was pushed into the syringe to load the column. The first bed-volume of eluent was saved as Waste One (W1). The following eluent was reloaded to the column until the whole batch has passed through it three times. The eluent of the final pass was saved as Flow-through One (FT1). The column was then washed with two bed-volumes of PBS and the eluent was saved as Flow-through Two (FT2). A further four bed-volumes of PBS was added to wash column and the eluent was saved as Waste Two (W2). A 50 mL syringe with plunger removed was connected to the column and loaded with 100 mM glycine solution at pH2.7. Elution of bound MAb5.2 was performed by pushing the glycine solution through the column with the plunger. A total of ten fractions, at one bed-volume/fraction, were saved. Each fraction was immediately neutralized with 50–135 $\mu$L 1M Tris solution, depending on the column capacity. The neutralized MAb5.2 fractions were stored at 4° C. The column was washed with three bed-volumes of dH$_2$O followed by the same volume of 20% ethanol. The column was stored at 4° C.

The success of MAb5.2 purification process was monitored by the presence of only two protein bands in SDS-PAGE under reducing condition. The two major bands at –30 kDa and –50 kDa represent the light chain and heavy chain of IgG, respectively. The purified MAb5.2 preparation was subsequently used for immuno-affinity column construction, Western blot analyses, and ELISA.

5. Protein Content Determination

The working dye reagent was prepared by diluting one part of the Dye Reagent Concentrate with four parts of ddH$_2$O. Twenty microlitres of protein sample or protein standard was mixed with 1 mL of the working dye reagent. The mixture was incubated at room temperature for 15 minutes. For the determination of immunoglobulin (Ig)-like proteins, bovine gamma-globulin (Bio-Rad, Hercules, Calif.) was used as standard. For other proteins, bovine serum albumin (BSA; Fraction V, Sigma, St. Louis, Mo.) was used instead. Optical density at 595 nm (OD$_{595}$) was measured either by a spectrophotometer, with the samples loaded into disposable cuvettes (Sarstedt), or by a microplate reader, with the samples loaded into framed PolySorp polystyrene Nunc-Immuno® Modules (Nunc InterMed).

Example 10

Purification of MSP1$_{42}$ By Immuno Affinity Chromotography

1. Preparation of MAb5.2 Immunoaffinity Column

MAb5.2 was coupled to CNBr-activated Sepharose® 4B (Pharmacia Biotech, Uppsala, Sweden) according to the manufacturer's instruction . All solutions were filtered through 0.45 $\mu$m pore-size membrane filter (Millipore) before use. The MAb5.2-coupled gel was packed into a glass Econo-Column chromatography column (Bio-Rad) and stored in 20% ethanol at 4° C.

2. Purification of Recombinant MSP1$_{42}$ Protein by MAb5.2 Immuno-affinity Column.

MAb5.2-coupled Sepharose 4B was prepared for immunoaffinity purification of the MSP1$_{42}$ protein as described above. Hemolymph sample, which was four-fold diluted in the starting buffer (PBS with an extra supplement of 1M NaCl), was loaded onto a 1 cm×5 cm column (Bio-Rad) packed with 3.5 mL MAb5.2-coupled Sepharose 4B gel. After washing the gel with eight bed-volumes of starting buffer (Waste), adsorbed proteins were eluted with six bed-volumes of 0.1M glycine solution, pH2.7. A total of six eluted fractions (E1 to E6), each equivalent to one bed volume, were collected. Each eluted fraction was neutralized immediately with 135 $\mu$L 1M Tris solution (pH 10.80) and then dialysed against dH$_2$O for gel electrophoresis. The SDS-PAGE results showed that MSP1$_{42}$ protein could be effectively purified from all contaminating hemolymph proteins. Some smaller proteins were observed to be associated with the purified MSP1$_{42}$ protein, and they may be breakdown products of MSP1$_{42}$ as they also showed up in the Western blot. On detailed observation of the band patterns, the purified PfMSP-1$_{42}$ protein was made up of two species with a slight difference in MW inserts). The efficiency of the MAb5.2 immunoaffinity column in purifying PfMSP-1$_{42}$ protein is summarized in Table 1.

TABLE 1

Efficiency of the MAb5.2 immunoaffinity column in purifying the recombinant MSP1$_{42}$ protein.

| Trial No. | Total PfMS-1$_{42}$ protein loaded ($\mu$g)* | Yield of PfMSP-1$_{42}$ protein in eluted fractions# | % Recovery |
|---|---|---|---|
| 1st | 508.8 | 188.0 | 37.0 |
| 2nd | 793.6 | 341.1 | 43.0 |

*as determined by sandwich ELISA.
total yield from the first two eluted fractions.

3. N-terminal Amino Acid Sequencing

MAb5.2 immunoaffinity-purified recombinant MSP1$_{42}$ protein was first transferred to a 0.2 $\mu$m pore-size PVDF membrane. The bound polypeptide was sequenced by auto Edman sequencing chemistry in a Hewlett® Packard HP G1005A Protein Sequencing System. Amino acid sequence was determined by calibrating with phenylthiohydantoin (PTH)-amino acid standards. The N-terminal amino acid sequence of the recombinant MSP1$_{42}$ protein was determined. The sequence obtained matches with the expected sequence. The sequencing result confirmed that the honeybee melittin signal peptide was correctly cleaved at the expected site and a secretory recombinant MSP1$_{42}$ was generated.

4. Glycan Test by DIG Glycan Detection Kit

Glycosylation of recombinant PfMSP-1$_{42}$ protein was examined by the DIG Glycan Detection Kit (Boehringer Mannheim, USA) according to the manufacturer's instruction. Briefly, SDS-PAGE was used to resolve the purified recombinant PfMSP-1$_{42}$ protein and the control proteins (provided by the kit). The proteins separated on the gel were transferred to a PVDF membrane. Glyco-conjugates of the proteins were then oxidized by a metaperiodate-bisulphite mixture. Subsequently, digoxigenin-succinyl-$\epsilon$-aminocaproic acid-hydrazide was added to probe the oxidized glyco-conjugates. The free binding sites of the membrane were blocked and the membrane was then incubated with the AP-conjugated anti-digoxigenin antibody provided. Finally, color development was performed according to the method mentioned above. The results indicated that recombinant MSP1$_{42}$ was glycosylated.

Example 11

Antibody Analysis

1. Indirect ELISA

Protein samples and protein standards (purified YMSP-1$_{19}$ [Kaslow D. C., Hui G., and Kumar S. (1994) Expression and Antigenicity of Plasmodium falciparum Major Merozoite Surface Protein (MSP119) Variants Secreted from Saccharomyces cerevisiae. Molecular and Biochemical Parasitology 63: 283–9. (Kaslow et al., 1994)] or recombinant PfMSP-1$_{42}$) at various concentration were diluted in ELISA coupling buffer and were coated onto 96-well MaxiSorp polystyrene plates (Nalge Nunc International) at 100$\mu$L/well at 4° C. for 16–24 hours. The plates were flicker-dried and washed three times (five minutes each) with 200 $\mu$L/well of blocking buffer. Sites on the plates were then saturated with 200 $\mu$L/well of saturation buffer at room temperature for one hour. After saturation, the plates were flicker-dried and washed three times (five minutes each) with 200 μL/well of wash buffer. Monoclonal antibody MAb5.2, diluted in saturation buffer (0.1 μg/mL; 100 μL/well), was added and the plates were incubated at room temperature for one hour. The plates were flicker-dried and washed five times (five minutes each) with 200 μL/well of blocking buffer. EIA-grade affinity purified goat-anti-rabbit IgG (H+L) HRP-conjugate (Bio-Rad, Hercules, Calif.) was diluted 2000-fold in secondary antibody buffer and pipetted into the wells at 100 μL/well. The plates were then incubated at room temperature for one hour. Finally, the plates were flicker-dried and washed three times (five minutes each) with blocking buffer and then twice (five minutes each) with wash buffer, at 200 μL/well. The HRP substrate mix was added at 100 μL/well and colour development was perfonned by incubating the plates at 37° C. for 20 minutes. Optical density at 405 nm ($OD_{405}$) was measured by a microplate reader (Molecular Devices or Bio-Rad). Blanks were included in the plates in which all antigens and antibodies were omitted except the respective buffers.

2. Sandwich ELISA

MAb5.2 diluted in ELISA coupling buffer (0.5 μg/mL; 100 μL/well) was coated onto 96-well MaxiSorp polystyrene plates (Nalge Nunc International) at 4° C. for 16–24 hours. The plates were washed and saturated as described above. Samples and standards were loaded onto the plate at 100 μL/well. Antigen capture was carried out at room temperature for one hour. Afterward, the plates were flicker-dried and washed three times (five minutes each) with 200 μL/well of wash buffer. Rabbit antisera against recombinant $MSP1_{42}$ protein was diluted 128,000-fold in saturation buffer and pipetted into the plates at 100 μL/well. The plates were incubated at room temperature for one hour. Afterward, the plates were then flicker-dried and washed five times (five minutes each) with 200 μL/well of blocking buffer. The subsequent incubation with goat-anti-rabbit IgG (H+L) HRP-conjugate, washings, colour development, and measurement of $OD_{405}$ readings were the same as in indirect ELISA.

3. Standardization of Response Curve in Sandwich ELISA

Since the sandwich ELISA is intended to be used to quantify the expression level of recombinant $MSP1_{42}$ protein, the response of the purified recombinant protein in this assay was first studied to provide a reference for further quantitation experiments. Serially diluted purified recombinant $MSP1_{42}$ protein was captured by MAb5.2 coated on ELISA plates. Anti-$MSP1_{42}$ or anti-MSP1-19 antiserum (the later one was previously raised in rabbits against a yeast-expressed recombinant MSP1-19 protein; 5,000-fold diluted in saturation buffer) was added into separate plates to determine the level of captured antigens as described before in the sandwich ELISA. The response of the two antisera toward the purified recombinant $MSP1_{42}$ was similar. Since the MSP1-19 protein is derived from the carboxyl terminal of the $MSP1_{42}$ protein, the similarity in response of the two antisera indicates that both preparations are specific to the common epitopes on both protein species. Because of this, the anti-MSP1-19 and anti-$MSP1_{42}$ antisera can be used in the sandwich ELISA interchangeably.

4. Competitive Inhibition ELISA

To determine if the conformation of the recombinant $PfMSP-1_{42}$ protein is similar to that of the carboxyl terminal of native PfMSP-1 protein, a competitive inhibition ELISA was performed. Since it is impractical to culture malarial parasites for the preparation of native PfMSP-1 protein, yeast-expressed $PfMSP-1_{19}$ proteins (YMSP-1-19 proteins) were used as a substitute for the PfMSP-1 protein. It has been shown previously (Kaslow et al., 1994) that the $YMSP-1_{19}$ proteins approximate the conformation of the carboxyl terminal of native PfMSP-1 protein.

In the present assay, only the E-TSR variant form of the $YMSP-1_{19}$ proteins was used. Anti-PfMSP-1 antisera (which were previously raised in rabbits K103 and K104 immunized with native PfMSP-1 protein) and MAb5.2 were each serially diluted and added to $YMSP-1_{19}$ protein-coated ELISA plates for indirect ELISA to obtain the respective titration curves against the $YMSP-1_{19}$ protein. The dilution of the antibody or antiserum that gave an ELISA activity falling within the mid-point of its titration curve was recorded. The antibody and antisera were then diluted accordingly and each of them was separately mixed with different concentration of inhibitors ($YMSP-1_{19}$ protein or recombinant $PfMSP-1_{42}$ protein). The mixtures were allowed to incubate at room temperature for one hour. Afterward, they were added to $YMSP-1_{19}$ protein-coated ELISA plates and indirect ELISA was performed as described before.

Competitive inhibition ELISA measures the reduction in reactivity of an antibody to an antigen (which was coated onto an ELISA plate) in the presence of various concentrations of an inhibitor. If the inhibitor has a conformation similar to the antigen, it will compete for the binding sites on the antibody and lead to a decrease in the reactivity of the antibody toward the antigen. An inhibition curve showing such a change in reactivity can thus be generated. By comparing the inhibition curve with the one using the antigen (in free form) as inhibitor, an estimation of the similarity in conformation of the two molecules can be obtained. This assay was employed in the present study to prove that the recombinant $PfMSP-1_{42}$ protein possesses the same conformation as in the carboxyl terminal of native PfMSP-1 protein.

Since it is impractical to culture the malarial parasites in large quantity to extract the PfMSP-1 protein for immunoassays, a series of four yeast-expressed recombinant $PfMSP-1_{19}$ proteins ($YMSP-1_{19}$ proteins) representing the different natural-occurring variant forms of the $PfMSP-1_{19}$ fragment were used as a substitute for the native PfMSP-1 protein. All four $YMSP-1_{19}$ proteins have been shown to possess the conformation of the same region of native PfMSP-1 protein. Since the recombinant $PfMSP-1_{42}$ protein carries the E-TSR variant-specific amino acid substitution at its carboxyl terminal, the corresponding $YMSP-1_{19}$ variant was used in the competitive inhibition ELISA. In the present study, the $YMSP-1_{19}$ protein was used as the antigen and it was first coated onto an ELISA plate. The free form of the $YMSP-1_{19}$ protein and the recombinant $PfMSP-1_{42}$ protein were separately used as inhibitors to compete for the binding sites of three antibody preparations, namely the anti-PfMSP-1 antisera from rabbits K103 and K104 (previously immunized with native PfMSP-1 protein) and the monoclonal antibody MAb5.2. The free $YMSP-1_{19}$ protein could completely inhibit the binding of MAb5.2 to the coated $YMSP-1_{19}$ protein. Similarly, a high level (>90%) of inhibition was obtained when the recombinant $PfMSP-1_{42}$ protein was used as the inhibitor. In addition, the inhibition curves of the two inhibitors differ by no more than one order of magnitude. In the case of the two anti-PfMSP-1 antisera, the extent of inhibition with $YMSP1_{19}$ protein as inhibitor was also similar to that with the recombinant $PfMSP-1_{42}$ protein. The present results indicate that the recombinant $PfMSP-1_{42}$ protein could effectively inhibit the binding of anti-PfMSP-1 and MAb5.2 antibodies to the $YMSP1_{19}$ protein; suggesting that the antibodies recognized common epitopes on both YMSP-1$_{19}$ and recombinant PfMSP-1$_{42}$ proteins. Since the three antibodies used in the present study have been shown to recognize the conformational epitopes on the carboxyl terminal of native PfMSP-1 protein [Chang S. P., Case S. E., Gosnell W. L., Hashimoto A., Kramer K. J., Tam L. Q.,Hashiro C. Q., Nikaido C. M., Gibson H. L., Lee-Ng C. T., Barr P. J., Yokota B. T., and Hui G. S. N. (1 996) A Recombinant Baculovirus 42-Kilodalton C-Terminal Fragment of Plasmodium falciparum Merozoite Surface Protein 1 Protects Aotus Monkeys Against Malaria. Infection and Immunity64(1): 253–61. (Chang et al., 1992)], the similar behaviour of the three antibody preparations toward YMSP-1$_{19}$ and PfMSP-1$_{42}$ proteins indicates that the three-dimensional structure of the recombinant PfMSP-1$_{42}$ protein should be similar to that of the native protein.

5. Immunogenicity Tests

A. Rabbit Immunization With Recombinant PfMSP-1$_{42}$ Protein

Four New Zealand White rabbits (7857, 7858, 7859 and 7860) were immunized with immunoaffinity-purified recombinant MSP1$_{42}$ protein. Four separate immunizations were given intramuscularly at three-week intervals. Each injection consisted of 100 µg recombinant MSP1$_{42}$ protein in complete Freund's adjuvant (Sigma, St. Louis, Mo.). The amount of mycobacterium in CFA was successively halved in each of the subsequent immunizations. Serum samples were collected one week before immunization as preimmune controls and 21 days after each immunization. Serum samples were tested for antibodies to MSP1$_{42}$.

End point titers for the 4 rabbits against different antigens after a secondary injection and a third injection. The antibodies show strong reactivity to the conserved region of MSP1$_{42}$ with minor reactivity to the non-conserved sequences (ETSR, EKNG, QKNG). The results indicate that the injection of purified MSP1$_{42}$ produced by the methods of this invention produces a highly specific immune response. In addition, the results indicate that the antibodies resulting from injecting the MSP1$_{42}$ produced by the methods of this invention all have consistently high titers. The consistency of the antibodies indicates that the MSP1$_{42}$ of the invention is an ideal vaccine product.

B. In Vitro Parasitic Growth Inhibition Assay

Rabbit anti-MSP1$_{42}$ sera were evaluated for their ability to inhibit blood stage malaria parasite growth in vitro. The preimmune sera as well as the tertiary and quartemary antisera were tested in the inhibition assay. Rabbit sera were heat inactivated at 58° C. for 40 minutes and absorbed with fresh normal human erythrocytes before use. Parasite cultures were synchronized by sorbitol lysis to select for late trophozoite and schizont stages. Infected erythrocytes were adjusted to a parasitemia of around 0.1% and a haematocrit of 0.8% by the addition of fresh human erythrocytes. The rabbit preimmune or immune sera were added to a final concentration of 15%, and 200-µL samples of the culture suspension were added in duplicate wells to a 96-well microtiter plate. The cultures were incubated at 37° C. in a 2% O$_2$, 8% CO$_2$, 90% N$_2$ gas mixture atmosphere for 72 hours. Duplicate wells of each sample were pooled, the cells were pelleted by centrifugation, thin blood smears were prepared, and the percentage parasitemia was determined microscopically. The degree of growth inhibition was calculated as follow:

Percentage inhibition=[(P-O)-(I-O)]/(P-O)×100% where P is the parasitemia at 72 hours of cultures incubated in preimmune sera, I is the parasitemia at 72 hours of cultures incubated in immune sera, and O is the initial starting parasitemia at 0 hour.

The tertiary and quaternary bleeds of anti-PfMSP-1$_{42}$ antisera were tested for their abilities in inhibiting parasite growth in vitro. Parasitized erythrocytes were treated with rabbit pre-immune sera or rabbit anti-PfMSP-14$_2$ antisera. After a 72-hour incubation period, the erythrocytes were harvested and Giemsa-stained for thin blood smear preparation. The blood smears were then used for parasite-inhibition determination and the results are tabulated in Table 2. As indicated, the anti-PfMSP-1$_{42}$ antisera were clearly effective in inhibiting parasitic growth. The inhibitory activity was already quite prominent in the tertiary antisera and after the third booster, the sera from all four rabbits could inhibit the propagation of the parasites by 89 to 96%.

TABLE 2

In vitro parasitic growth inhibition assay using rabbit anti-PfMSP-1$_{42}$ antisera.

| Rabbit | Parasite Count | | % Growth Inhibition[#] |
|---|---|---|---|
| | Pre-bleed | Antiserum-treated | |
| Tertiary Bleed at Day 20 (3d20) | | | |
| 7857 | 189* | 44 | 81% |
| 7858 | 151 | 21 | 92% |
| 7859 | 149 | 47 | 73% |
| 7860 | 170 | 85 | 53% |
| Quaternary Bleed at Day 18 (4d18) | | | |
| 7857 | 211* | 36 | 89% |
| 7858 | 178 | 20 | 96% |
| 7859 | 194 | 29 | 94% |
| 7860 | 201 | 33 | 90% |

*Number of parasites per 1,000 RBC at 0 hour = 10
*Number of parasites per 1,000 RBC at 0 hour = 14

C. Specificity of Anti-PfMSP-1$_{42}$ Antibody Response

The amino acid sequence of the MSP-1$_{19}$ fragment (the C-terminal 19 kDa region of MSP1-42) is conserved among different isolates of *Plasmodium falciparum*, in which only four amino acid substitutions were observed. In the first EGF-like domain of PfMSP-1$_{19}$, amino acid 1644 (notated with reference to the PfMSP-I protein) is either Q or E; while in the second EGF-like domain, amino acids 1691–1701 have been found to be either TCTEEDSGSSR ([SEQ ID NO:10 ( referred to as TSR variant) or KCT-EEDSGSNG [SEQ ID NO:11 (referred to as KNG variant)].

The four variant forms of PfMSP1$_{19}$ fragment have been expressed in yeast (referred as YMSP1$_{19}$ proteins) and proven to possess the conformation as in the carboxyl-terminal of native PfMSP-1 protein (Kaslow et al., 1994). These YMSP-1$_{19}$ proteins (except the Q-TSR variant) were used in the present study to examine the specificity of the anti-PfMSP-1$_{42}$ antibody responses. The specificity was manifested by the end-point titers of the antisera to the three variant forms of YMSP-1$_{19}$ proteins. As shown in FIG. 59, the overall anti-PfMSP-1$_{42}$ antibody responses of all four immunized rabbits to the three YMSP-1$_{19}$ proteins were similar, except a higher response to the E-TSR variant form than to the other two was observed at a later stage of immunization. The similarity in antibody responses toward different variant forms of YMSP-1$_{19}$ protein indicates that the majority of the anti-PfMSP-1$_{42}$ antibody responses were targeted toward the common epitopes of the different YMSP-1$_{19}$ proteins and these epitopes were immunogenic. The result also suggests that the rabbit antisera raised against the recombinant PfMSP-1$_{42}$ protein were cross-reactive against the PfMSP-1$_{42}$ produced by different isolates of *Plasmodium falciparum*.

Example 12

In Vitro Expression of Recombinant PfMSP-1$_{42}$ Protein

The time course of MSP1$_{42}$ expression was studied by a sandwich ELISA as mentioned bove. BmN cells were infected with each of the recombinant BmNPVs at low and high MOI (MOI=1 and 10 respectively). Among the three recombinant viruses, only BmNPV-sp42 gave a significant level of PfMSP-1$_{42}$ expression. As the PfMSP-1$_{42}$ protein could be detected in the culture medium the honeybee melittin signal peptide in this construct appeared to be correctly processed in generating a secretory product. The maximal level of expression in BmNPV-sp42-infected cells was observed four days after infection at both MOI. However, a higher yield of the protein was obtained with BmN cells infected at low MOI. On the contrary, the expression level of the other two recombinant BmNPVs (BmNPV-p42 and BmNPV-hp42) was extremely low. Detectable level of the PfMSP-1$_{42}$ protein expressed by BmNPV-p42 was only observed around three to four days after infection but not at days 1–2 or 5–6 post infection.

Example 13

In Vivo Expression of Recombinant PiMSP-1$_{42}$ Protein

The time course of PfMSP-1$_{42}$ expression in silkworms, the in vivo host of BmNPV, was examined. 3.6×10$^5$ pfu of recombinant BmNPV were injected into each silkworm to commence the infection process. Over a period of six to seven days, the infected silkworms were sacrificed daily and their hemolymph collected for assay.

The result of the in vivo. expression studies was similar to the in vitro one. Only BmNPV-sp42 produced a significant level of expression. The expression profiles of the three recombinant BmNPVs was determined. For BmNPV-sp42, the expression of MSP1$_{42}$ protein in the hemolymph could be detected three days after infection. The expression level dramatically increased from day 5 to day 6 and reached a maximum on day 7. However, the silkworms on day 7 were heavily infected and were close to dying. For the other two recombinant viruses, the. expression of MSP 1$_{42}$ was delayed (from day 4 onward) and the final yields were much lower than that of BmNPV-sp42.

The presence of MSP1$_{42}$ protein in BmNPV-sp42-infected hemolymph was further confirmed by Western blot analysis. A clear signal of the MSP1$_{42}$ protein was unequivocally observed. In contrast, there was no prominent increase of the corresponding protein band in the silver-stained gel. This was probably due to the fact that the recombinant MSP1$_{42}$ protein only constitutes 0.54% of the total hemolymph protein. As for the other two recombinant viruses, their expression levels, in terms of percentage of total protein, were estimated to be 0.005% for BmNPV-p42 and 0.004% for BmNPV-hp42. Because of this, it is obvious that no signals could be detected from them in Western blotting, even when more samples were applied.

Example 14

Northern Hybridization

The great difference in MSP1$_{42}$ expression levels among the three recombinant BmNPVs indicates the possibility of a deviation in the control mechanism of protein expression. Northern blot analysis was thus performed to resolve if this could be accounted for at the transcriptional level. BmN cells were separately infected with each recombinant BmNPV at a MOI of one and were harvested four days after infection (the day maximal recombinant MSP1$_{42}$ protein expression level was achieved). Total RNA of the infected cells was isolated for Northern hybridization in which a radioactive PfMSP-1$_{42}$-specific DNA probe was used to detect the presence of PfMSP-1$_{42}$ transcripts. The results showed a single band of the expected size (~1620 bases) of the PfMSP-1$_{42}$ transcript was detected in the RNA sample isolated from BmN cells infected with any one of the recombinant BmNPVs. By comparing the band intensity, the PfMSP-1$_{42}$ transcript levels of the three recombinant BmN-PVs differed only at most by two to three folds. As the expression levels of the PfMSP-1$_{42}$ protein differed by more than 100 fold, it is unlikely that transcriptional regulation could solely account for this huge difference. The present result suggests that translational control may play a more prominent role in dictating the expression of the recombinant PfMSP-1$_{42}$ protein in the three recombinant BmNPVs.

Example 15

Purification of BmNPV-Expressed Recombinant MSP1$_{42}$ Protein

Various chromatographic media have been tried to evaluate their suitability in purifying the recombinant MSP1$_{42}$ protein from hemolymph of infected silkworms. These media included Superose 12 (Pharmacia), Streamline™ SP (Pharnacia), POROS HS/M (PE Biosystems), Hydroxylapatite (Bio-Rad), SOURCE™ 30Q (Pharmacia), Mono Q HR 5/5 (Pharmacia), Q-Sepharose Fast Flow (Pharmacia), ConA Sepharose (Pharmacia), and Blue Sepharose 4B (Pharmacia). With the exception of POROS HS/M which was used with the BioCAD® 700E Perfusion Chromatography® Workstation (PE Biosystems), all chromatographic separations were performed on the FPLC system LCC 500 (Pharmacia). In addition, protein purification by ammonium sulphate precipitation and immunoaffinity purification using MAb5.2-coupled Superose 4B was evaluated for the mentioned purpose. All elution buffers were filtered by 0.45 μm pore-size membrane filtration before use. Insoluble materials in the hemolymph were removed by centrifuging at 13,000 rpm at 4° C. for 20 minutes before samples were loaded onto columns.

1. Ammonium Sulphate Precipitation

The use of ammonium sulphate precipitation was first evaluated as a crude step in purifying the MSP1$_{42}$ protein from hemolymph. Hemolymph sarnple was ten-fold diluted in ddH$_2$O. An equal volume of a saturated ammonium sulphate solution was slowly added to the diluted hemolymph to precipitate proteins at a final concentration of 50% ammonium sulphate. Further precipitation of hemolymph protein was performed at higher concentrations of ammonium sulphate . The protein precipitates and their respective soluble fractions were harvested separately. Each protein precipitate was resuspended in 1 mL ddH$_2$O. Afterward, all harvested samples were dialyzed against dH$_2$O to remove ammonium sulphate. SDS-PAGE and Western blot analyses were then performed to analyse the dialysed samples. As indicated by Western blotting, the MSP1$_{42}$ protein was first precipitated at 50% ammonium sulphate and almost completely precipitated when the concentration was increased to 60%. Unfortunately, the amount of contaminating proteins also increased concomitantly and a trace of the MSP1$_{42}$ protein still remained in the soluble fraction. In view of these results, ammonium sulphate precipitation appears to be ineffective in enriching the MSP1$_{42}$ protein.

2. Superose 12 (Size-Exclusion)

Superose 12 was tried to fractionate the $MSP1_{42}$ or $PfMSP1_{42}$ protein from hemolymph proteins. Two hundred microlitres of hemolymph was first made up to 500 μL with PBS and loaded onto a prepacked Superose 12 HR 10/30 column (10 mm×30 cm; Pharmacia). Proteins were eluted with PBS and the elution profile was obtained by monitoring the optical density of each eluted fraction at 280 nm ($OD_{280}$). The presence of the $PfMSP-1_{42}$ protein was first detected by a sandwich ELISA as described above, in which the anti-$PfMSP1_{19}$ antibody was used to probe the captured $PfMSP-1_{42}$ protein. Fractions from the major ELISA-reactive peak of four independent runs were pooled and concentrated by ultrafiltration (UltraFree®-MC 10,000 NMWL filter units, Millipore). 0.5 mL of the concentrated material was reloaded onto the same column for a second round of purification. A major and a minor ELISA-positive peak were observed. Pooled fractions corresponding to these two ELISA peaks were separately concentrated and analysed by SDS-PAGE and Western blotting. A weak Western blot signal was detected in the minor peak with a corresponding molecular weight lower than expected. However, the major ELISA-reactive fractions did not show any signal. In the silver-stained gel, the major hemolymph proteins were still present in the major ELISA-reactive fractions. Based on these observations, chromatography in Superose 12 is ineffective in separating the $PfMSP-1_{42}$ protein from hemolymph proteins.

3. Streamline™ SP (Strong Cation Exchanger)

Streamline™ SP cation exchanger is a chromatographic medium designed for expanded bed adsorption chromatography. The protein to be purified can be recovered in an eluted fraction after the direct application of a crude feedstock onto the column without the need of removing particulate materials in the feedstock (Pharmacia Biotech). The omission of sample pre-treatment before loading makes expanded bed chromatography an attractive method in purifying the $PfMSP-1_{42}$ protein from bulk silkworm hemolymph samples.

Two hundred microlitres of hemolymph containing protease inhibitors (Complete Protease Inhibitor Cocktail Tablet from Roche, Germany), at a ratio of one tablet to 50 mL hemolymph, was made up to 1 mL in buffer A (20 mM sodium phosphate, pH6.0) and loaded onto a 2.5 cm×10 cm column (Bio-Rad) packed with 20 mL Streamline™ SP gel. The column was washed with buffer A to remove unadsorbed materials. Adsorbed proteins were then eluted with 1M NaCl in buffer A. Sandwich ELISA was performed to examine the elution of $PfMSP-1_{42}$ protein and two reactive peaks were obtained: one in the flow-through and the other in the 1M NaCl fractions. The $PfMSP-1_{42}$ protein was found to be present in both ELISA-reactive peaks by Western blotting. However, in terms of specific activity ($PfMSP-1_{42}$ protein to total hemolymph protein), the flow-through fraction was much less "reactive". Though the 36 kDa hemolymph protein was not completely removed from the 1M NaCl fractions, other proteins of higher MW were significantly reduced. In view of these results, the use of Streamline™ SP can be considered as a first step in purifying the $PfMSP-1_{42}$ protein from hemolymph.

4. POROS HS/M (Strong Cation Exchanger)

Perfusion chromatography was tried to purify the $PfMSP-1_{42}$ protein because it can rapidly separate a target protein from its contaminants in a matter of minutes, thus reducing the chances of protein degradation. In the present study, the POROS HS/M chromatographic medium was evaluated. The $PfMSP-1_{42}$ protein was adsorbed by the POROS HS/M gel at pH 4.2 and 5 but not at higher pH, e.g. 7.5. As a preliminary trial, the sample pH was adjusted to 4 for loading. Two hundred micrograms of immunoaffinity-purified $PfMSP-1_{42}$ protein was made up to 2 mL in 20 mM ammonium acetate, pH4.0 and loaded onto a prepacked 4.6 mm×100 mm POROS HS/M column (PE Biosystems; bed volume: 1.7 mL). Adsorbed materials were eluted with a gradient of 0 to 1M NaCl and a pH gradient of 4–6. Each eluted fraction was neutralized immediately with 100PL 1M Tris, pH9.6. The sandwich ELISA profile of the chromatogram showed two major reactive peaks: one in the ~0.3M NaCl fractions and the other in the 1M NaCl fractions. Since the predominant protein in the sample loaded was $PfMSP-1_{42}$ protein purified by immunoaffinity chromatography, the presence of two peaks suggests that two immuioreactive species may be present. Indirect ELISA, in which the eluted fractions were directly coated onto ELISA plates for assay, was performed to examine if any difference in ELISA reactivity would occur. A much higher reactivity was detected in the 1M NaCl fractions in indirect ELISA. In addition, two ELISA-reactive peaks were detected in the fractions eluted at ~0.3M NaCl. To resolve this, the indirect ELISA-reactive fractions were selected for SDS-PAGE and Western blot analyses. The result of Western blotting clearly showed that the $PfMSP-1_{42}$ protein was eluted only in the presence of 1M NaCl at a pH higher than 4. As there was no prominent Western blot signal around the 42 kDa range, the two ELISA-reactive peaks associated with the ~0.3M NaCl fractions were probably due to immunoreactive fragments or aggregates of the $PfMSP-1_{42}$ protein.

The above purification process was repeated by loading a larger sample of hemolymph (500 μL, diluted ten-fold with 20 mM ammonium acetate, pH4.0; to the column. Sandwich ELISA was used to monitor the elution profile of the $PfMSP-1_{42}$ protein and three reactive peaks were detected; one in the ~0.3M NaCl fractions and two in the 1M NaCl fractions. In indirect ELISA, a similar profile was obtained. As in the first experiment, Western blotting showed that the $PfMSP-1_{42}$ protein was eluted only in the presence of 1M NaCl at a pH higher than 4. Materials in the fractions corresponding to the first ELISA peak were composed of immunoreactive protein fragments of around 23 kDa.

Integration of the $OD_{280}$ profile of the chromatogram showed that almost 90% of the total hemolymph protein could be removed from the $PfMSP-1_{42}$ protein in the 1M NaCl peak. In view of the speed of purification and the purity of the product obtained, the POROS HS/M column was further evaluated to determine the optimal conditions for the purification of $PfMSP-1_{42}$ protein. Hemolymph was ten-fold diluted in 20 mM ammonium acetate, pH4.0 with 1M NaCl. Protease inhibitors (Complete protease inhibitor cocktail tablet from Roche, Germany) were then added. Two millilitres of this diluted hemolymph sample was loaded onto the same POROS HS/M column and eluted with a pH gradient of 4–6. After reaching pH 6, elution was continued using a gradient of 0 to 1M NaCl . The fractions were neutralized immediately with 100 μL 1M Tris, pH 9.6. Indirect ELISA and Western blot results showed that the $PfMSP-1_{42}$ protein could not be eluted at pH6 unless NaCl was present. To maximize recovery, the optimal elution condition for the $PfMSP-1_{42}$ protein in POROS HS/M was set at pH6 and 1M NaCl.

5. Hydroxyapatite (Anion Exchanger)

Hydroxylapatite $(Ca_5(PO4)_3OH)_2$ is a form of calcium phosphate which can be used for separating and purifying proteins, enzymes, nucleic acids, viruses, and other macromolecules. Owing to its anion-exchanging property, hydroxylapatite was also tried for purifying the $PfMSP-1_{42}$ protein.

One hundred microlitres of hemolymph was made up to 500 μL in 10 mM sodium phosphate, pH7.0. The sample was loaded onto a 1 cm×10 cm column (Bio-Rad) packed with 3 mL hydroxylapatite gel (DNA-grade Bio-Gel® HTP gel). After washing the medium with buffer A (dH$_2$O), adsorbed proteins were eluted with a gradient of buffer B (1M sodium phosphate, pH7.0). Sandwich ELISA result showed two major reactive peaks; one at the end of the flow-through and the other at 25% buffer B. In Western blot analysis, the PfMSP-1$_{42}$ protein was detected only in the 25% buffer B fractions. Unfortunately, the major hemolymph proteins were still associated with the PfMSP-1$_{42}$ protein. Therefore, hydroxylapatite appears to be an ineffective medium for the purification of PfMSP-1$_{42}$ protein.

6. SOURCE™ 30Q (Strong Anion Exchanger)

Taking the advantages of high sample capacity and ability to withstand high flow rate, SOURCE™ 30Q was examined to see if it could purify the PfMSP-1$_{42}$ protein efficiently. Four millilitres neat hemolymph with protease inhibitors (Complete protease inhibitor cocktail tablet from Roche, Germany) at a concentration as mentioned above was loaded onto a XK 16/20 column (Pharmacia) prepacked with 20 mL SOURCE™ 30Q gel. After washing the column with buffer A (10 mM Tris, pH8.0), adsorbed proteins were eluted at different concentrations of NaCl. By sandwich ELISA, major immunoreactive peaks could be observed at 0, 0.1 and 0.2M NaCl. The spread of signals at different concentrations of NaCl was thought to be due to sample overloading. Because of this, the experiment was repeated with half of the amount of hemolymph. However, similar elution and sandwich ELISA profiles were obtained. The indiscriminant presence of PfMSP-1$_{42}$ protein in different fractions was further confirmed by Western blot analysis. This observation suggests that protein-protein interactions between the PfMSP-1$_{42}$ protein and other hemolymph proteins may be a predominant phenomenon, and such interactions may be substantial enough to affect the ionic interactions between the chromatographic medium and the PfMSP-1$_{42}$ protein. In view of these results, SOURCE™ 30Q is not a suitable medium for purifying the PfMSP-1$_{42}$ protein from hemolymph.

7. MonoQ HR 5/5 (Strong Anion Exchanger)

One hundred microlitres of the hemolymph was made up to 500 μL in buffer A (10 mM Tris, pH8.0) and loaded onto a prepacked MonoQ HR 5/5 column (5 mm×50 mm; Pharmacia). Adsorbed proteins were eluted with a gradient of 0 to 1M NaCl in buffer A. The sandwich ELISA profile showed a prominent signal in the 0.1M NaCl fractions. By Western blot analysis, a signal corresponding to the PfMSP-1$_{42}$ protein was detected only in the 1M NaCl fractions and nothing could be observed in the 0.1M NaCl ones. Though the PfMSP-1$_{42}$ protein was detected in the 1M NaCl fractions, the protein content of these fractions was very low and no band corresponding to the protein was observable in the silver-stained gel. Since the capacity of the MonoQ column used was relatively low, this column appears to be more suitable for purifying the PfMSP-1$_{42}$ protein at a later stage of the fractionation scheme when less amount of proteins are encountered.

8. Q-Sepharose Fast Flow (Strong Anion Exchanger)

Q-Sepharose Fast Flow was also evaluated in the purification of PfMSP-1$_{42}$ protein. Three hundred microlitres of hemolymph was made up to 1 mL in buffer A (10 mM Tris, pH8.0) and loaded onto a 1 cm×10 cm column (Bio-Rad) packed with 4 mL Q-Sepharose Fast Flow gel. Adsorbed proteins were eluted with a step-gradient of increasing NaCl concentration in buffer A. By sandwich ELISA and Western blot analysis, the PfMSP-1$_{42}$ protein was found to be eluted at 0.2M NaCl. The SDS-PAGE result showed that the active fractions were essentially free of major contaminating proteins, except for the presence of a 36 kDa band. Moreover, a protein doublet band with a size very close to the PfMSP-1$_{42}$ protein was seen in the active fractions. Though ELISA reactive, the 1M NaCl fraction gave no signal in Western blot analysis. With the effective removal of high MW contaminating proteins, Q-Sepharose Fast Flow appears to be a suitable medium for purifying the PfMSP-1$_{42}$ protein.

9. ConA Sepharose (Affinity)

The recombinant PfMSP-1$_{42}$ protein was shown to be glycosylated as described above. Because of this, ConA Sepharose (which is used for purifying glycoproteins) was tried to see if it would be suitable for purifying this protein. Hemolymph was diluted ten-fold in the starting buffer (25 mM Tris, pH7.5 containing 0.5M NaCl) and 1 mL of it was loaded onto a 1 cm×5 cm column (Bio-Rad) packed with 1 mL ConA Sepharose gel. Unadsorbed materials were washed out with six bed-volumes of starting buffer. Afterward, the adsorbed proteins were eluted with nine bed-volumes of elution buffer (starting buffer containing 0.5M methyl-α-D-glycopyranoside). Western blotting result showed that the majority of the PfMSP-1$_{42}$ protein was not adsorbed, while a very small portion of it was eluted in 0.5M methyl-α-D-glycopyranoside. In light of this observation, some PfMSP-1$_{42}$ proteins may be glycosylated. According to the SDS-PAGE result, most of the high MW proteins in the hemolymph could be effectively removed from the PfMSP-1$_{42}$ protein in the flow-through fractions. In view of this, ConA Sepharose may also be suitable for purifying the PfMSP-1$_{42}$ protein.

10. Blue Sepharose 4B (Affinity)

One hundred microlitres of hemolymph was made up to 500 μL in buffer A (10 mM Tris, pH8.0) and loaded onto a 1 cm×10 cm column (Bio-Rad) packed with 3.5 mL Blue Sepharose 4B gel. Adsorbed proteins were eluted in a gradient of 0 to 1M NaCl in buffer A. By sandwich ELISA, a single reactive peak was observed in the flow-through fraction. As indicated in the silver-stained SDS-PAGE gel, the 36 kDa contaminating hemolymph protein was almost completely removed. Unfortunately, many other proteins were still present in this fraction. In contrast to the ELISA result, no signal could be detected in all of the ELISA-positive fractions by Western blotting. Because of these conflicting observations, we decided Blue Sepharose 4B is not a suitable medium for purifying the PfMSP-1$_{42}$ protein.

11. Combination of Chromatographic Separations

Based on the results obtained in the initial trials of different chromatographic media, we have tried to combine some of them in sequence and examine if a protocol can be developed for the purification of PfMSP-1$_{42}$ protein. The following are two such protocols we have evaluated. In both protocols, cation-exchange chromatography using POROS HS/M gel was chosen as the first step because it has fast flow rate and good discriminating power.

12. POROS HS/M and Q-Sepharose

Ten millilitres of hemolymph, which was diluted four-fold in buffer A (20 mM sodium phosphate buffer, pH 6.0), was loaded onto a 1.5 cm×10 cm column (Bio-Rad) packed with 9 mL POROS HS/M gel. Chromatography was performed in a FPLC system LCC 500 (Pharmcia). The column was washed with buffer A and adsorbed proteins were eluted in a single step with 1M NaCl. By Western blot analysis, the PfMSP-1$_{42}$ protein was confirmed to be in the 1M NaCl fraction. The 1M NaCl fractions were pooled and dialysed against 10 mM Tris, pH8.0 at 4° C. overnight. The soluble proteins were loaded onto a 2.5 cm×10 cm column (Bio-Rad) packed with 20 mL Q-Sepharose gel. The column was eluted with a step gradient of 0, 0.1, 0.2, 0.3 and 1.0M NaCl. Although fractions collected at 0.2 and 0.3M NaCl were positive in the Western blot, no distinctive $PfMSP-1_{42}$ band was observed in the corresponding silver-stained gel. On the contrary, the $PfMSP-1_{42}$ protein was detectable by both silver-staining and Western blotting in the 1M NaCl fraction. However, the protein was still not completely purified as some high MW proteins were still present. The yield and fold of purification of the $PfMSP-1_{42}$ protein are summarized in Table 3 below.

TABLE 3

Recovery of recombinant $PfMSP-1_{42}$ protein from infected hemolymph after purifying from POROS HS/M and Q-Sepharose.

| | Total $PfMSP-1_{42}$ protein present (μg)* | Total protein content (mg)# | Specific activity (mg $PfMSP-1_{42}$ protein: mg total protein content) | Fold of protein purification@ |
|---|---|---|---|---|
| 1/4 diluted starting infected hemolymph | 5600 | 55.44 | 0.101 | 1 |
| POROS HS/M 1M NaCl fraction | 1710 | 15.84 | 0.108 | 1.07 |
| Q-Sepharose 1M NaCl fraction | 243.75 | 1.33 | 0.183 | 1.81 |

*as determined by sandwich ELISA.
as determined by Bradford assay (Bio-Rad).
@values referred to the specific activity of the starting infected hemolymph.

13. POROS HS/M, ConA Sepharose and Q-Sepharose

Eight millilitres of hemolymph diluted four-fold in buffer A (20 mM sodium phosphate buffer, pH6.0) was processed by POROS HS/M chromatographic medium. The NaCl concentration of the active fraction was adjusted to 0.5M by addition of $dH_2O$ and the pH to 7.5 by adding 1M Tris buffer, pH9.6. The fraction was then loaded onto a 1.5 cm×10 cm column (Bio-Rad) packed with 10 mL ConA Sepharose gel. Proteins adsorbed were eluted as described above. The results from SDS-PAGE and Western blot analyses were essentially similar to that described above; the $PfMSP-1_{42}$ protein was mainly eluted in the flow-through, while a small portion of it was eluted in 0.5M methyl-α-D-glycopyranoside. In an attempt to further purify the protein, the flow-through fraction from ConA Sepharose was concentrated and loaded onto a Q-Sepharose column (2.5 cm×10cm, 20 mL packed gel). Adsorbed proteins were eluted with a step-gradient of 0, 0.15, 0.2, 0.3 and 1.0M NaCl. SDS-PAGE and Western blotting results showed that the $PfMSP-1_{42}$ protein was distributed non-discriminantly in various fractions. No further purification could be achieved in this last step. The yield and fold of purification of the $PfMSP-1_{42}$ protein at different stages are summarized in Table 4 below.

TABLE 4

Recovery of recombinant $PfMSP-1_{42}$ protein from infected hemolymph after purifying successively from POROS HS/M, ConA Sepharose and Q-Sepharose.

| | Total $PfMSP-1_{42}$ protein present (μg)* | Total protein content (mg)# | Specific activity (mg $PfMSP-1_{42}$ protein: mg total protein content) | Fold of protein purification@ |
|---|---|---|---|---|
| 1/4 diluted starting infected hemolymph | 6944 | 76.96 | 0.09 | 1 |
| POROS HS/M 1M NaCl fraction | 1944 | 29.43 | 0.07 | 0.78 |
| ConA Sepharose flow-through fraction 2 | 982.8 | 8.33 | 0.12 | 1.33 |
| Q-Sepharose 0.15M NaCl fraction | 55.8 | 0.33 | 0.17 | 1.89 |

*as determined by sandwich ELISA.
as determined by Bradford assay (Bio-Rad).
@values referred to the specific activity of the starting infected hemolymph.

Example 16

Production of Biologically Active Recombinant $PfMSP-1_{42}$ Protein as Revealed by Disulphide Bond Reduction Disulphide bond formation in the recombinant $PfMSP-1_{42}$ protein was examined by resolving the protein in SDS-PAGE under reducing (with β-mercaptoethanol, β-ME) and non-reducing (without β-ME) conditions. The non-reduced $PfMSP-1_{42}$ protein migrated as a 45 kDa polypeptide and the mobility of the protein was decreased after reduction. The apparent MW of the reduced protein increased from 50 to 56 kDa as the final percentage of β-ME was increased from 2.5 to 10%. Western blot analysis showed that the reactivity of the $PfMSP-1_{42}$ protein to MAb5.2 was lost dramatically after reduction. This indicates that proper disulphide bond formation was essential to antigenicity.

Example 17

Expression of Recombinant $PfMSP-1_{42}$ Protein

The three recombinant BmNPVs were used to infect BmN cells and silkworms for $PfMSP-1_42$ protein expression. To quantify the protein, a sandwich ELISA was developed (as described above). The sandwich ELISA was sensitive enough to detect as little as three nanograms of the $PfMSP-1_{42}$ protein. Using this assay, the BmNPV-sp42 was found to be the only recombinant BmNPV that gave a high expression level (in vitro: 5.28 μg/6×10$^5$ cells infected for four days at MOI=1; in vivo: 378.86 μg/mL hemolymph infected for seven days). On the other hand, an extremely low expression level was obtained from the BmNPV-p42 (in vitro: 9.52 ng/6×10$^5$ cells infected for three days at MOI=10; in vivo: 1.54 μg/mL hemolymph infected for six days) and the BmNPV-hp42 (in vitro: undetectable; in vivo: 2.07 g/mL hemolymph infected for six days). Since the DNA sequence of $PfMSP-1_{42}$ could be detected in all of the recombinant viruses by Southern hybridization, the extremely low expression level of BmNPV-p42 and BmNPV-hp42 cannot be due to the absence of the gene. The major differences in the three PfMSP-1$_{42}$ constructs were the presence of a signal peptide in the secretory PfMSP-1$_{42}$ construct and the joining sequence around the initiator AUG codon. Thus, the different nucleotide compositions at the 5' joint may be the cause of the huge difference in expression among the three constructs. To examine if transcriptional regulation would account for such a difference, BmN cells were infected with the recombinant BmNPVs and their PfMSP-1$_{42}$ mRNA measured by Northern hybridization. The difference in mRNA level as detected could not account for the huge difference in protein expression. Thus, neither transcriptional control nor mRNA stability could be used to explain the difference in expression of the three recombinant viruses. The expression of the PfMSP-1$_{42}$ protein is therefore likely to be regulated at the translational level. It has been recommended that monolayer insect cell culture be infected at high MOI (MOI$\geq$10) to synchronize the infection of cells for recombinant protein expression (O' Reilly D. R., Miller L. K., and Luckow V. A. Baculovirus Expression Vectors—A Laboratory Manual. New York: Oxford University Press, Inc., 1994.O' Reilly, 1994; Murphy C. I. and Piwnica-Worms H. Generation of Recombinant Baculoviruses and Analysis of Recombinant Protein Experssion. In: Ausubel F. M., Brent R., Kingston R. E., Moore D. D., Seidman J. G., Smith J. A., and Struhl K., eds, Current Protocols in Molecular Biology. USA: John Wiley & Sons, Inc., 1995; unit 16.11. ). However, the present in vitro expression studies demonstrate that the synchronization process is not a must and infection at low MOI (MOI=1) can give a higher yield of the protein. The enhanced yield may be attributed to the delayed decrease in insect cell viability upon infection at low MOI, which would otherwise result in rapid cell lysis and subsequently a lowered yield of the PfMSP-1$_{42}$ protein.

Despite the success in expressing the secretory form of PfMSP-1$_{42}$ protein at a moderately high level in vitro, the requirement of fetal bovine serum for BmN cell culture makes this method expensive to produce the protein. On the contrary, the natural host of BmNPV, the silkworm, is readily available in large quantity in Eastern and Southern China and the cost of rearing it is very low. With the introduction of an artificial diet, silkworms can now be reared all year-round. As in vivo expression of the PfMSP-1$_{42}$ protein was 107.6-fold higher than in vitro (378.86 μg/mL hemolymph vs 3.52 μg/mL culture medium), the use of silkworms to produce the PfMSP-1$_{42}$ protein appears to be the most cost-effective way in producing a vaccine for malaria.

We claim:

1. A method of producing a malaria immunogenic composition, comprising:
    (a) expressing an immunogenic fragment of MSP $1_{42}$ in a baculovirus expression system, wherein said expression system comprises one or more silkworms infected with a nuclear polyhedrosis virus, and wherein said silkworms comprise hemolymph;
    (b) collecting said hemolymph from said one or more silkworms and combining said hemolymph with a reducing agent;
    (c) purifying said immunogenic fragment from said hemolymph; and
    (d) formulating said immunogenic fragment in a malaria immunogenic composition.

2. The method of claim 1 wherein said immunogenic fragment is purified by chromatography or electrophoresis.

3. The method of claim 2 wherein said chromatography purification method is selected from the group consisting of ion exchange chromatogaphy; metal chelating affinity chromatography; molecular weight sieving, high pressure liquid chromatography, affinity chromatography and antibody affinity chromatography.

4. The method of claim 2 wherein said silkworm is *Bombyx mori* silkworm.

5. The method of claim 1 wherein said immunogenic composition includes an adjuvant.

6. The method of claim 5 wherein said adjuvant is selected from the group consisting of aluminum phosphate, aluminum hydroxide, saponin, Quil A, muramyl dipeptide, monophosphoryl lipid A muramyl tripeptide, cytokines, diphteriatoxoid, exotoxin A, granulocyte-macrophage colony stimulating factor and phospholipid conjugates.

7. The method of claim 1 wherein said immunogenic composition includes cholera toxin.

8. The method of claim 7 wherein said cholera toxin is choleratoxin subunit A or choleratoxin subunit B.

9. The method of claim 1 wherein said reducing agent comprises dithiothreitol (DTT).

10. The method of claim 1 wherein said reducing agent comprises beta-mercaptoethanol (β-ME).

* * * * *